(12) United States Patent
Slusser et al.

(10) Patent No.: US 12,109,099 B1
(45) Date of Patent: Oct. 8, 2024

(54) SURGICAL IMPLANT DELIVERY SYSTEM AND RELATED METHODS

(71) Applicant: Athena Surgical, LLC, Minnetonka, MN (US)

(72) Inventors: Greg Slusser, Excelsior, MN (US); Brian P. Beaubien, Saint Paul, MN (US); Vincent R. Lucente, Macungie, PA (US)

(73) Assignee: Athena Surgical, LLC, Minnetonka, MN (US)

( * ) Notice: Subject to any disclaimer, the term of this patent is extended or adjusted under 35 U.S.C. 154(b) by 717 days.

(21) Appl. No.: 17/013,355

(22) Filed: Sep. 4, 2020

(51) Int. Cl.
*A61F 2/00* (2006.01)
*A61B 17/06* (2006.01)
*A61B 90/00* (2016.01)
*A61B 17/00* (2006.01)

(52) U.S. Cl.
CPC ...... *A61F 2/0045* (2013.01); *A61B 17/06109* (2013.01); *A61B 90/06* (2016.02); *A61B 2017/00455* (2013.01); *A61B 2017/00805* (2013.01); *A61B 2090/062* (2016.02)

(58) Field of Classification Search
CPC ......... A61F 2/0045; A61B 2017/00805; A61B 17/00; A61B 90/06; A61B 17/06109; A61B 5/391
See application file for complete search history.

(56) References Cited

U.S. PATENT DOCUMENTS

| | | | |
|---|---|---|---|
| 5,112,344 A | 5/1992 | Petros | |
| 5,899,909 A | 5/1999 | Claren et al. | |
| 6,273,852 B1 | 8/2001 | Lehe et al. | |
| 6,491,703 B1 | 12/2002 | Ulmsten | |
| 6,494,887 B1 | 12/2002 | Kaladelfos | |
| 6,596,001 B2 | 7/2003 | Stormby et al. | |
| 6,612,977 B2 | 9/2003 | Staskin et al. | |
| 6,638,209 B2 | 10/2003 | Landgrebe | |
| 6,638,210 B2 | 10/2003 | Berger | |
| 6,641,525 B2 | 11/2003 | Rocheleau et al. | |
| 6,648,921 B2 | 11/2003 | Anderson et al. | |

(Continued)

FOREIGN PATENT DOCUMENTS

| | | |
|---|---|---|
| AT | 452596 | 1/2010 |
| AU | 697010 | 9/1998 |

(Continued)

OTHER PUBLICATIONS

Boston Scientific, "Advantage Fit and Advantage Transvaginal Mid-Urethral Sling Systems" Brochure, 2018.

(Continued)

*Primary Examiner* — Christine H Matthews
(74) *Attorney, Agent, or Firm* — Jonathan D. Spangler; Jay B. Bell

(57) ABSTRACT

An implant delivery system for delivering a surgical implant attached to a needle to a surgical target site is described. The implant delivery system comprises a handle body, handle insert, and a needle. The handle insert extends through the handle body and includes a proximal end configured to engage with the handle body and a distal end configured to engage the needle. The handle insert is rotatable between a first position in which the needle may be inserted or removed and a second position in which the needle is locked in place.

19 Claims, 20 Drawing Sheets

(56) References Cited

U.S. PATENT DOCUMENTS

| | | |
|---|---|---|
| 6,802,807 B2 | 10/2004 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,971,986 B2 | 12/2005 | Staskin et al. |
| 6,991,597 B2 | 1/2006 | Gellman et al. |
| 7,025,772 B2 | 4/2006 | Gellman et al. |
| 7,048,682 B2 | 5/2006 | Neisz et al. |
| 7,070,556 B2 | 7/2006 | Anderson et al. |
| 7,094,199 B2 | 8/2006 | Petros et al. |
| 7,112,210 B2 | 9/2006 | Ulmsten et al. |
| 7,204,802 B2 | 4/2007 | De Leval |
| 7,235,043 B2 | 6/2007 | Gellman et al. |
| 7,261,723 B2 | 8/2007 | Smith et al. |
| 7,267,645 B2 | 9/2007 | Anderson et al. |
| 7,288,063 B2 | 10/2007 | Petros et al. |
| 7,291,104 B2 | 11/2007 | Neisz et al. |
| 7,291,115 B2 | 11/2007 | Batke et al. |
| 7,297,102 B2 | 11/2007 | Smith et al. |
| 7,347,813 B2 | 3/2008 | Claren et al. |
| 7,364,541 B2 | 4/2008 | Chu et al. |
| 7,402,133 B2 | 7/2008 | Chu et al. |
| 7,611,454 B2 | 11/2009 | De Leval |
| 7,658,743 B2 | 2/2010 | Ulmsten |
| 7,762,969 B2 | 7/2010 | Gellman et al. |
| 7,867,161 B2 | 1/2011 | Staskin et al. |
| 7,972,262 B2 | 7/2011 | Rocheleau et al. |
| 7,988,615 B2 | 8/2011 | Anderson et al. |
| 8,007,452 B2 | 8/2011 | Gellman et al. |
| 8,012,080 B2 | 9/2011 | Chu et al. |
| 8,016,741 B2 | 9/2011 | Weiser et al. |
| 8,033,983 B2 | 10/2011 | Chu et al. |
| 8,097,007 B2 | 1/2012 | Evans et al. |
| 8,162,816 B2 | 4/2012 | Gellman et al. |
| 8,303,526 B2 | 11/2012 | Gellman et al. |
| 8,439,820 B2 | 5/2013 | MacLean et al. |
| 8,475,357 B2 | 7/2013 | Staskin et al. |
| 8,480,559 B2 | 7/2013 | Knapp et al. |
| 8,602,965 B2 | 12/2013 | Chu et al. |
| 8,617,048 B2 | 12/2013 | Gellman et al. |
| 8,628,463 B2 | 1/2014 | Ogdahl et al. |
| 8,632,453 B2 | 1/2014 | Chu et al. |
| 8,777,837 B2 | 7/2014 | Ogdahl et al. |
| 8,790,240 B2 | 7/2014 | Chu et al. |
| 8,814,777 B2 | 8/2014 | Gellman et al. |
| 8,828,092 B2 | 9/2014 | Toso et al. |
| 8,845,511 B2 | 9/2014 | Gellman et al. |
| 8,852,077 B2 | 10/2014 | Staskin |
| 8,858,578 B2 | 10/2014 | Chu et al. |
| 8,915,872 B2 | 12/2014 | Gellman et al. |
| 8,915,927 B2 | 12/2014 | Chu et al. |
| 8,926,495 B2 | 1/2015 | Chu et al. |
| 9,005,222 B2 | 4/2015 | Evans et al. |
| 9,078,728 B2 | 7/2015 | Chu |
| 9,089,396 B2 | 7/2015 | Browning |
| 9,149,261 B2 | 10/2015 | Chu et al. |
| 9,226,810 B2 | 1/2016 | Chu |
| 9,375,302 B2 | 6/2016 | Ogdahl et al. |
| 9,433,488 B2 | 9/2016 | Gellman et al. |
| 9,554,886 B2 | 1/2017 | Chu et al. |
| 9,655,706 B2 | 5/2017 | Toso et al. |
| 9,655,708 B2 | 5/2017 | Chu |
| 9,693,801 B2 | 7/2017 | Allen |
| 9,717,580 B2 | 8/2017 | Anderson et al. |
| 9,775,699 B2 | 10/2017 | Jenkins et al. |
| 9,872,750 B2 | 1/2018 | Evans et al. |
| 9,939,813 B2 | 4/2018 | Chu et al. |
| 9,968,428 B2 | 5/2018 | Lund et al. |
| 9,974,639 B2 | 5/2018 | Chu |
| 9,980,801 B2 | 5/2018 | Ogdahl et al. |
| 10,039,626 B2 | 8/2018 | Chu |
| 10,105,160 B2 | 10/2018 | Ogdahl et al. |
| 2002/0091298 A1 | 7/2002 | Landgrebe |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Chu et al. |
| 2002/0156489 A1 | 10/2002 | Gellman et al. |
| 2003/0009181 A1 | 1/2003 | Gellman et al. |
| 2003/0045892 A1 | 3/2003 | Kaladelfos |
| 2004/0073234 A1 | 4/2004 | Chu et al. |
| 2004/0087970 A1 | 5/2004 | Chu et al. |
| 2004/0116944 A1 | 6/2004 | Chu et al. |
| 2004/0225181 A1 | 11/2004 | Chu et al. |
| 2005/0101973 A1 | 5/2005 | Smith et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0261545 A1 | 11/2005 | Gellman et al. |
| 2008/0139877 A1 | 6/2008 | Chu et al. |
| 2008/0281148 A1 | 11/2008 | Evans et al. |
| 2009/0069628 A1 | 3/2009 | Chu et al. |
| 2009/0240261 A1* | 9/2009 | Drews .................. A61B 17/322 606/133 |
| 2010/0287761 A1 | 11/2010 | Gellman et al. |
| 2010/0312044 A1 | 12/2010 | Neisz et al. |
| 2011/0112358 A1 | 8/2011 | Gellman et al. |
| 2011/0301409 A1 | 12/2011 | Chu et al. |
| 2011/0301410 A1 | 12/2011 | Gellman et al. |
| 2012/0016370 A1 | 1/2012 | Chu et al. |
| 2012/0215063 A1 | 8/2012 | Holsten et al. |
| 2013/0303839 A1 | 11/2013 | Gellman et al. |
| 2014/0121454 A1 | 5/2014 | Mamo et al. |
| 2014/0303431 A1 | 10/2014 | Suslian et al. |
| 2015/0011822 A1 | 1/2015 | Evans |
| 2015/0080645 A1 | 3/2015 | Gellman et al. |
| 2016/0022401 A1 | 1/2016 | Chu et al. |
| 2016/0038179 A1* | 2/2016 | Rao .................. A61B 17/00234 600/37 |
| 2016/0051354 A1 | 2/2016 | Patankar et al. |
| 2017/0340319 A1* | 11/2017 | Viola ............... A61B 17/06109 |
| 2018/0071070 A1 | 5/2018 | Evans et al. |
| 2018/0153672 A1 | 6/2018 | Browning |
| 2018/0243069 A1 | 8/2018 | Chu |

FOREIGN PATENT DOCUMENTS

| | | |
|---|---|---|
| AU | 704712 | 4/1999 |
| AU | 2002219041 | 5/2002 |
| AU | 2003259834 | 7/2004 |
| AU | 2002254144 | 6/2006 |
| AU | 2002254157 | 7/2006 |
| AU | 2006222727 | 10/2008 |
| AU | 2003259819 | 2/2009 |
| AU | 2004291049 | 9/2009 |
| AU | 2003269964 | 10/2009 |
| AU | 2009217434 | 10/2009 |
| AU | 2010224358 | 10/2010 |
| AU | 2004233885 | 11/2010 |
| AU | 2008249151 | 10/2011 |
| BR | PI0416483 | 1/2016 |
| CA | 2198778 | 5/2003 |
| CA | 2510570 | 7/2004 |
| CA | 2231155 | 3/2005 |
| CA | 2440153 | 9/2011 |
| CA | 2523580 | 3/2012 |
| CA | 2495314 | 7/2012 |
| CA | 2439212 | 2/2014 |
| CA | 2495666 | 5/2014 |
| CA | 2705609 | 10/2016 |
| CN | 1083708 | 5/2002 |
| CN | 1119123 | 8/2003 |
| CN | 1515230 | 7/2011 |
| DE | 69618650 | 9/2002 |
| DE | 69519737 | 12/2003 |
| DE | 69633078 | 7/2005 |
| DE | 60312992 | 12/2007 |
| DE | 60223502 | 11/2008 |
| DE | 60325374 | 1/2009 |
| DE | 602004024819 | 2/2010 |
| DE | 60331358 | 4/2010 |
| DE | 60239188 | 3/2011 |

(56) References Cited

FOREIGN PATENT DOCUMENTS

| | | |
|---|---|---|
| DK | 0854691 | 4/2002 |
| DK | 0778749 | 6/2003 |
| DK | 1151722 | 8/2004 |
| DK | 1686921 | 4/2010 |
| EP | 0778749 | 12/2000 |
| EP | 0854691 | 1/2002 |
| EP | 1159921 | 1/2002 |
| EP | 1326540 | 7/2003 |
| EP | 1151722 | 8/2004 |
| EP | 1528898 | 4/2007 |
| EP | 1365679 | 11/2007 |
| EP | 1531737 | 12/2008 |
| EP | 1686921 | 12/2009 |
| EP | 1581148 | 2/2010 |
| EP | 1365688 | 1/2011 |
| EP | 2292182 | 3/2011 |
| EP | 1617767 | 9/2012 |
| EP | 1913896 | 12/2012 |
| EP | 2471468 | 2/2016 |
| EP | 1803415 | 6/2016 |
| ES | 2152423 | 2/2001 |
| ES | 2170880 | 8/2002 |
| ES | 2225405 | 3/2005 |
| ES | 2335669 | 3/2010 |
| HK | 1039739 | 3/2005 |
| JP | 3229327 | 11/2001 |
| JP | 3333519 | 10/2002 |
| JP | 2005535412 | 11/2005 |
| JP | 2008212703 | 9/2008 |
| JP | 4181410 | 11/2008 |
| JP | 2009045469 | 3/2009 |
| JP | 4298296 | 7/2009 |
| JP | 2010063901 | 3/2010 |
| JP | 4589867 | 12/2010 |
| JP | 5437323 | 3/2014 |
| JP | 5657225 | 1/2015 |
| KR | 20060129185 | 12/2006 |
| RU | 2161916 | 1/2001 |
| SE | 503271 | 4/1996 |
| SE | 506164 | 11/1997 |
| WO | 1996006567 | 3/1996 |
| WO | 1997013465 | 4/1997 |
| WO | 2002034124 | 5/2002 |
| WO | 2002058564 | 8/2002 |
| WO | 2002058565 | 8/2002 |
| WO | 2002062237 | 8/2002 |
| WO | 2002071931 | 9/2002 |
| WO | 2002071953 | 9/2002 |
| WO | 2003017848 | 3/2003 |
| WO | 2003075792 | 9/2003 |
| WO | 2003096930 | 11/2003 |
| WO | 2004012579 | 2/2004 |
| WO | 2004016180 | 4/2004 |
| WO | 2004060206 | 7/2004 |
| WO | 2004016196 | 12/2004 |
| WO | 2004096088 | 3/2005 |
| WO | 2005048879 | 12/2005 |
| WO | 2005122721 | 12/2005 |
| WO | 2007097994 | 8/2007 |
| WO | 2008033950 | 3/2008 |
| WO | 2008057261 | 5/2008 |
| WO | 2011022515 | 2/2011 |
| WO | 2013123036 | 8/2013 |
| WO | 2015060804 | 4/2015 |
| WO | 2015063407 | 5/2015 |
| ZA | 200604787 | 9/2007 |

OTHER PUBLICATIONS

Ethicon, "Gynecare TVT Abbrevo Continence System" Instructions for Use Brochure, 2009.
Ethicon, "Gynecare TVT Exact Continence System" Instructions for Use Brochure, 2009.
Ethicon, "Gynecare TVT Obturator System" Instructions for Use Brochure, 2005.

* cited by examiner

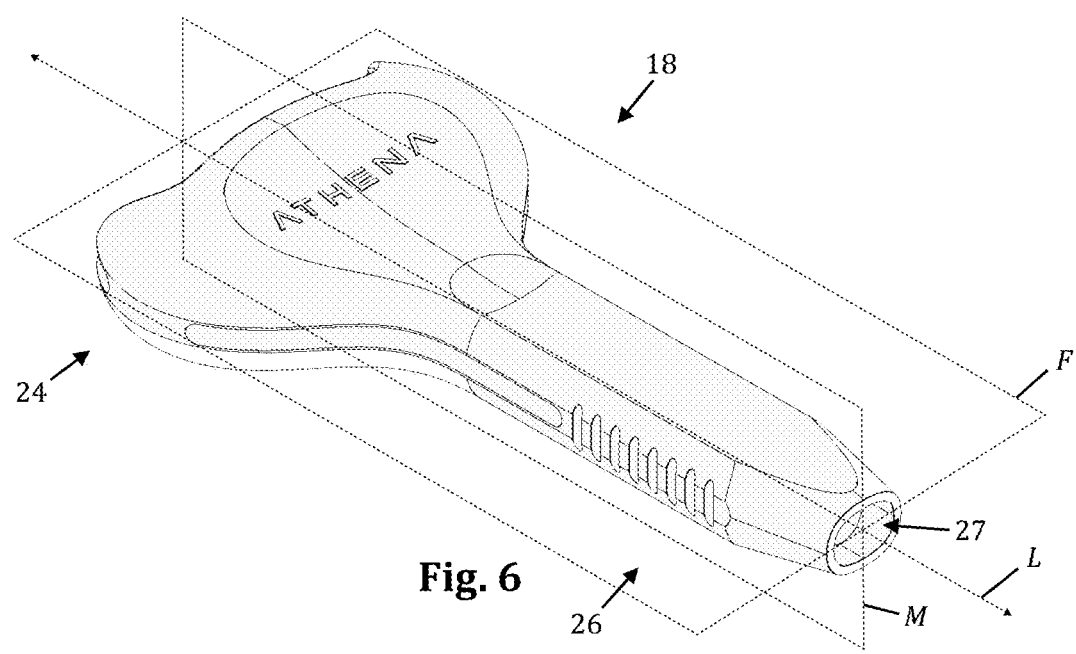
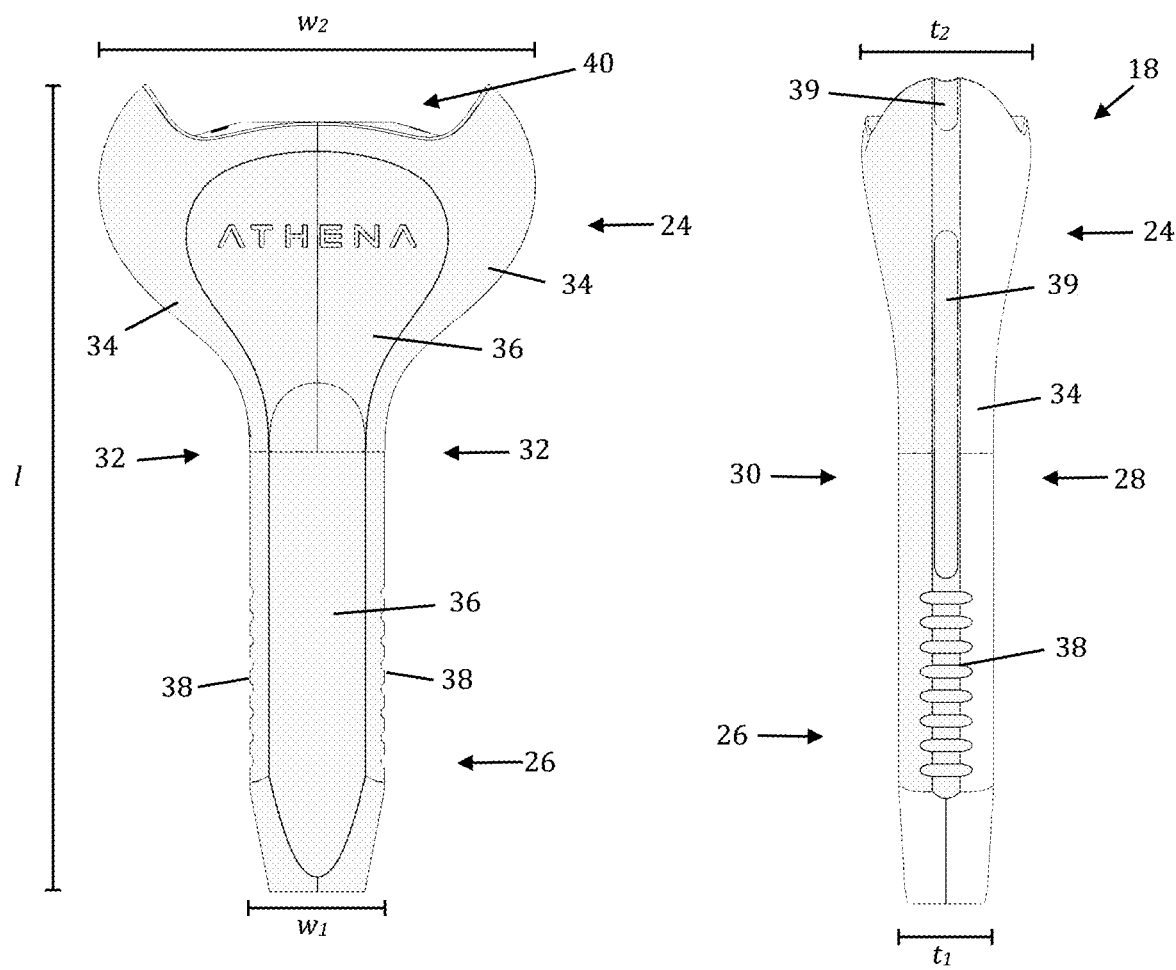
Fig. 6
Fig. 7
Fig. 8

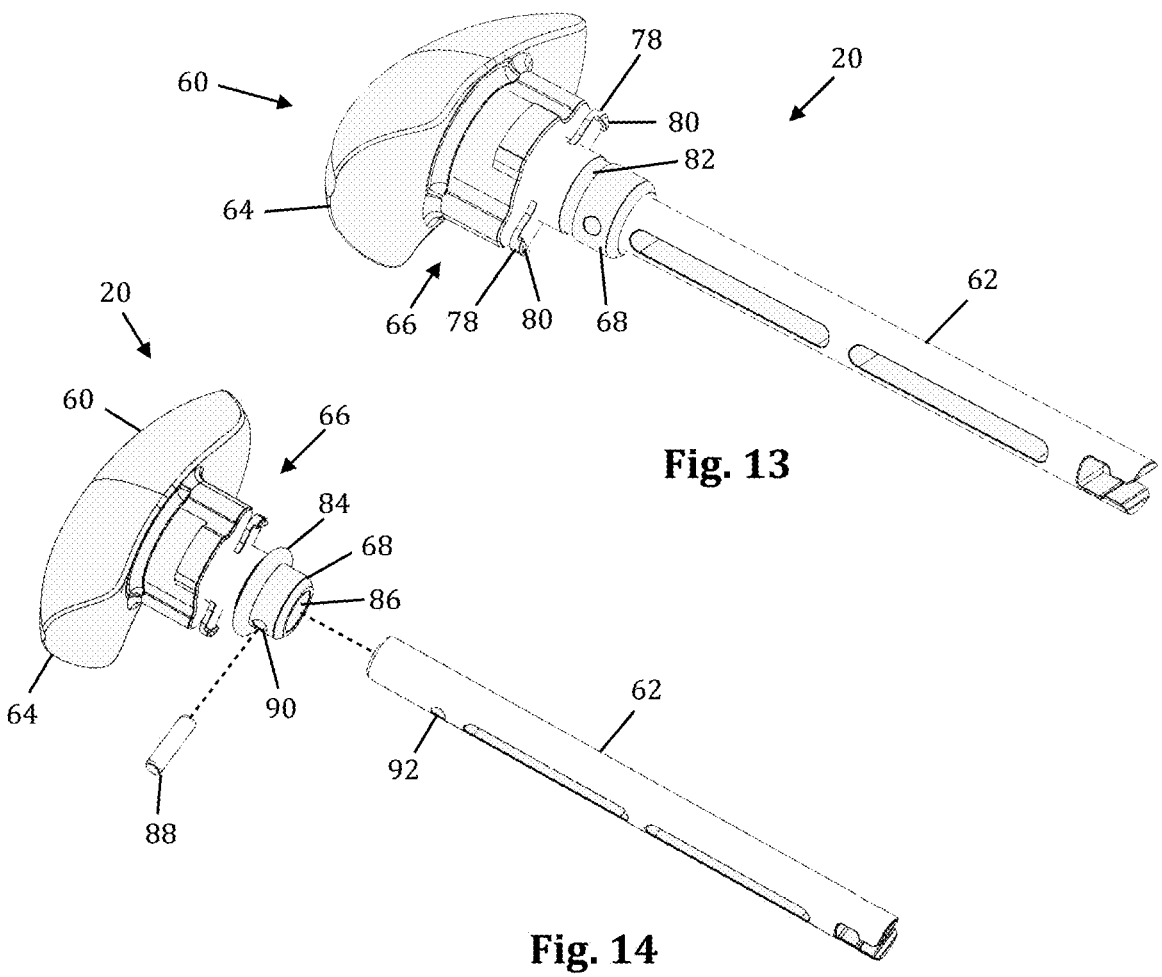
Fig. 13
Fig. 14
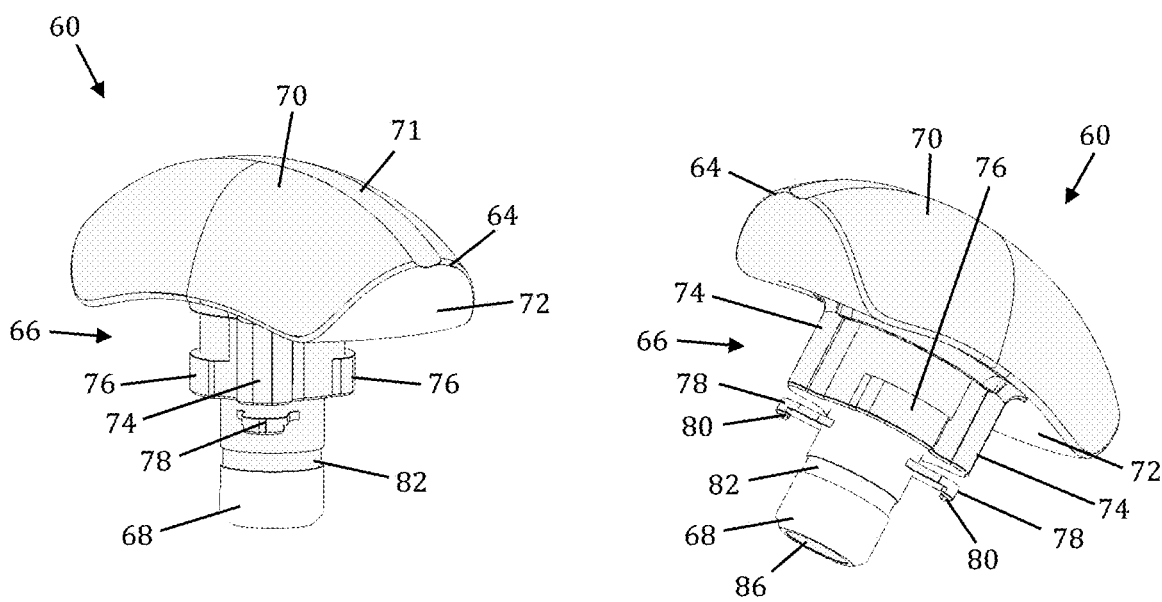
Fig. 15
Fig. 16

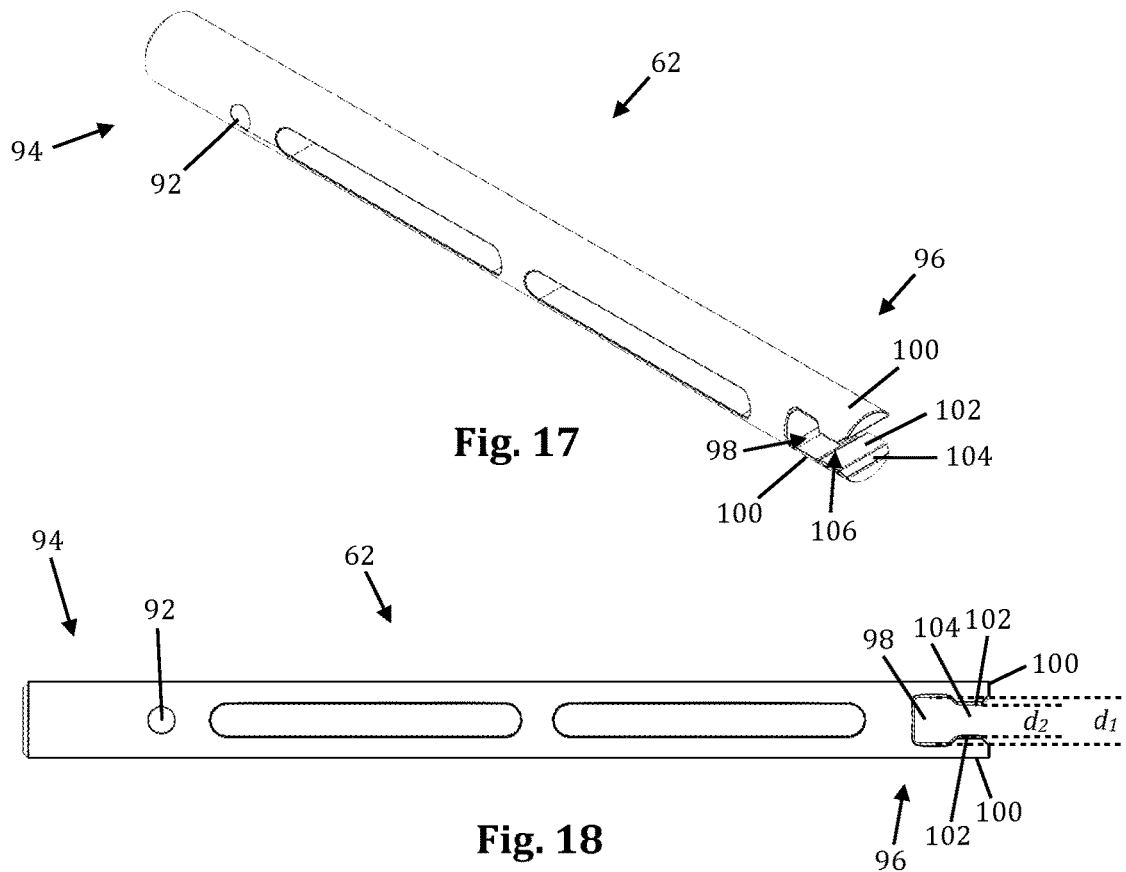
Fig. 17
Fig. 18
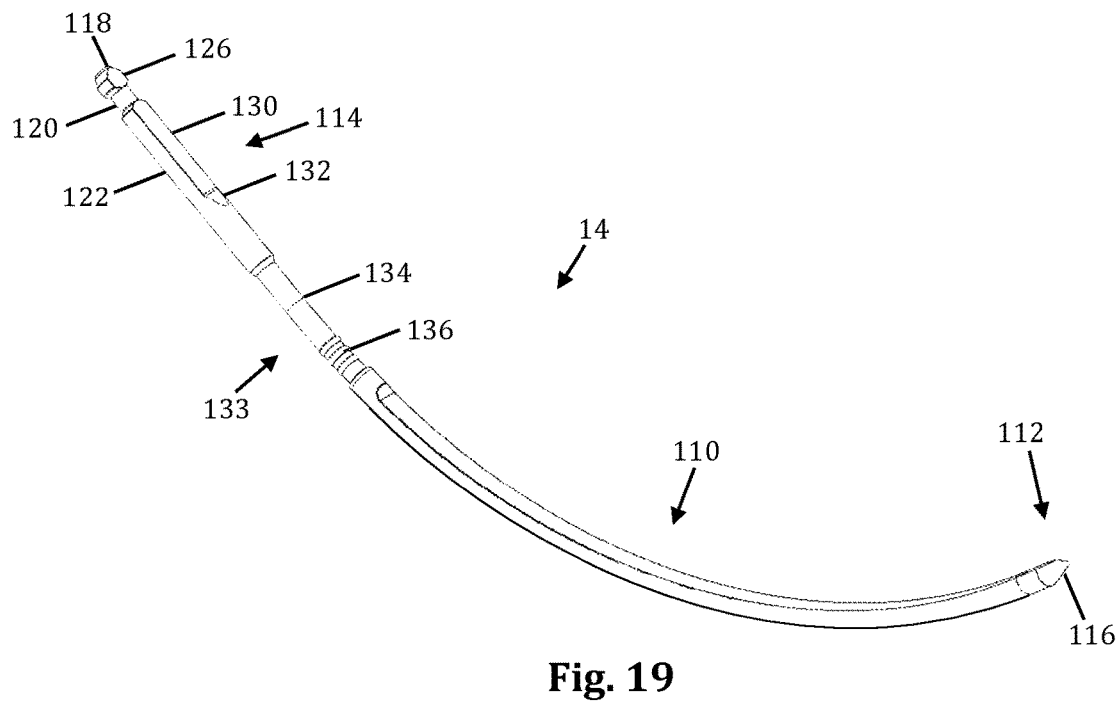
Fig. 19

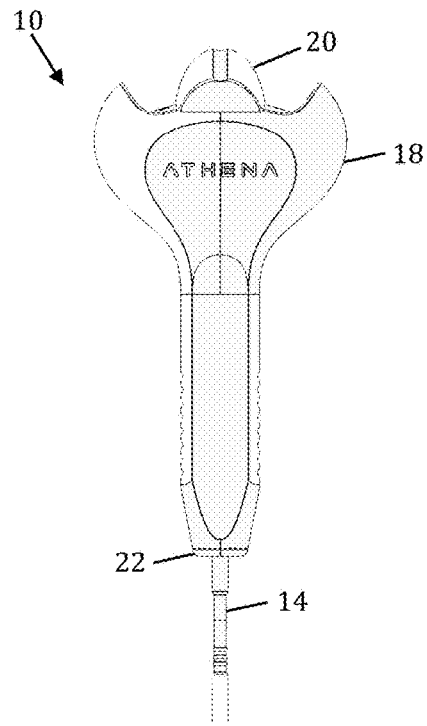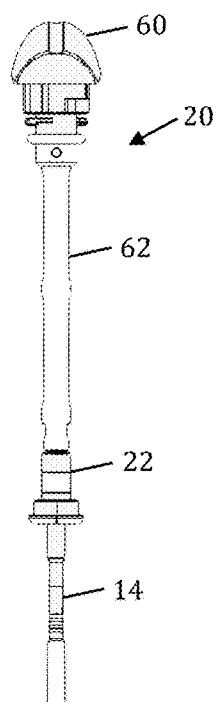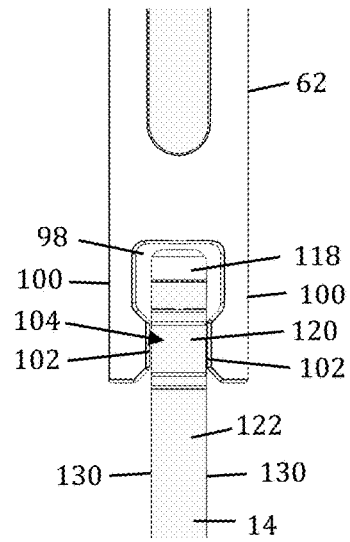
Fig. 28    Fig. 29    Fig. 30
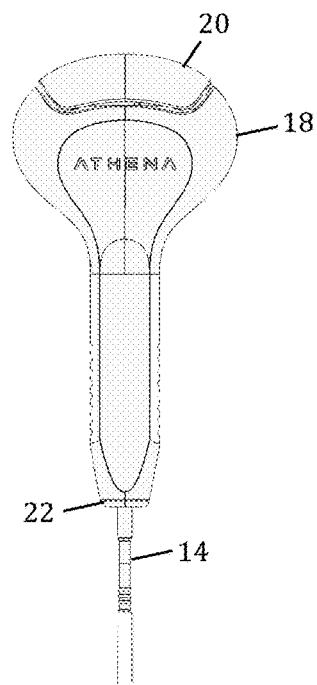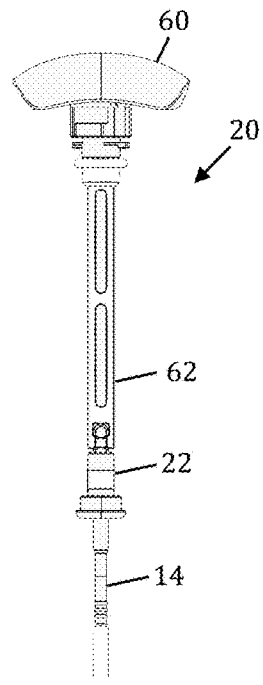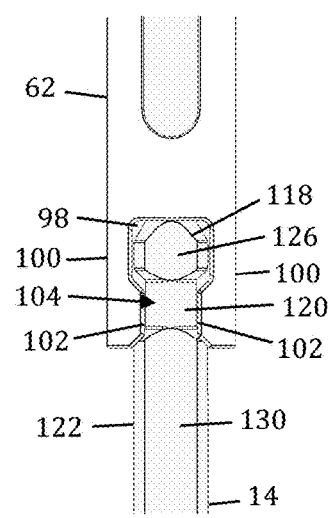
Fig. 31    Fig. 32    Fig. 33

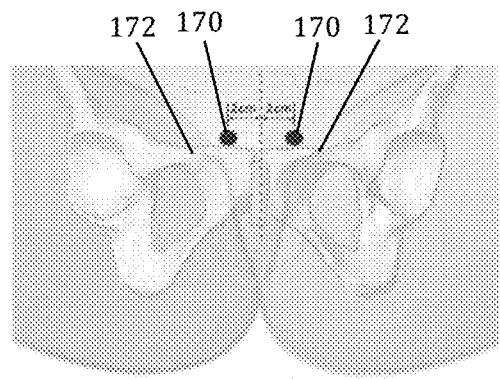
Fig. 36
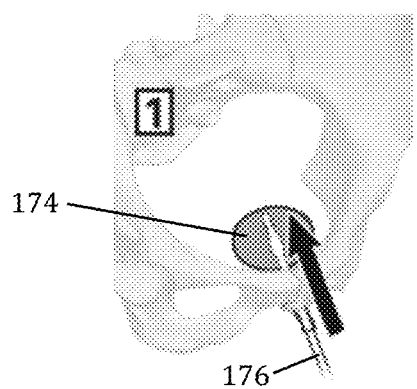 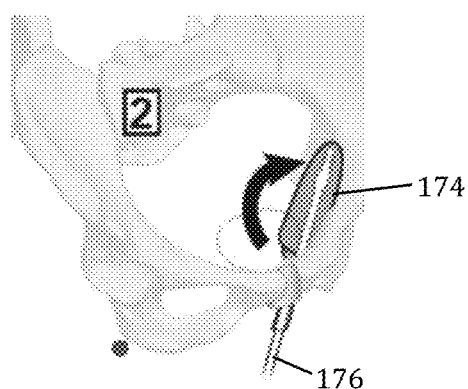
Fig. 37A　　　　　　　　Fig. 37B

SURGICAL IMPLANT DELIVERY SYSTEM AND RELATED METHODS

FIELD

The present disclosure relates generally to surgical procedures, and more specifically to needle-guided delivery of surgical implants to a surgical target site.

BACKGROUND

Urinary incontinence is the unintentional loss of bladder control, and can be a frustrating problem for millions of Americans. Not knowing when and where one might have an accident can affect everything from work to exercise to social life. Urinary incontinence affects both men and women, but is more common in women. The most common form of incontinence in women is stress urinary incontinence (SUI). SUI happens when there is stress or pressure on the bladder, for example when weak pelvic floor muscles put pressure on the bladder and urethra by making them work harder. Women who have SUI may often experience a loss of bladder control during normal daily activities that use the pelvic floor muscles such as laughing, coughing, sneezing, or exercising.

There are a few reasons why the pelvic floor muscles can lose strength: They may be stretched by weight gain, a sports injury, or pregnancies and vaginal childbirths. SUI can have a significant negative impact on the quality of life of not only those who suffer from the condition, but also potentially on those friends and family members whose lives and activities may also be limited. For example, women with incontinence have lower self-esteem, a less active sex life, and higher levels of depression than women with healthy bladders.

A number of treatment techniques (surgical and nonsurgical) have been developed to help treat female urinary incontinence. One surgical procedure is a sling procedure, for example a retropubic midurethral sling ("RMUS"). In this procedure, a needle or other implant-delivering device is inserted through the anterior vaginal wall below the pubic bone. The needle is guided through the subrapubic fascia around the urethra, behind and at least partially around the pubic bone, and out of the body through a small incision in the abdomen. Sutures and/or a surgical mesh (e.g., natural or synthetic) are attached to the needles and pulled through the body to support the urethra. The sutures and/or surgical mesh then remain in the body after the conclusion of the procedure.

One of the main challenges with a RMUS procedure is surgeon repeatability and reproducibility, in part because the RMUS procedure involves a curved needle guided by hand through delicate patient tissue. Surgeon repeatability and reproducibility is most dependent upon factors such as needle insertion depth, needle track and placement, and needle exit. Additionally, one of the most common complications with a RMUS procedure is bladder perforation in the form of a button hole puncture in the outer bladder tissue. Therefore, a need exists to provide instrumentation and technique for performing a RMUS procedure that is repeatable and reproducible, with minimal disruption to body tissue.

SUMMARY

The present disclosure overcomes some of these challenges by describing an implant delivery system configured to deliver an implant attached to a needle to a surgical target site. In some embodiments, the implant delivery system may include a handle assembly and a needle removably engaged with the handle assembly. The needle may be configured to engage with an implant, and is maneuverable by the handle assembly to guide the implant to a surgical target site within a patient. By way of example, the handle assembly may have an ergonomic shape designed to help the surgeon maintain proper alignment and positioning of the needle during insertion. The needle may have a generally flat surface that provides visibility to maintain a horizontal plain, tactile plain orientation with a finger placement on the flat, and an anatomical orientation when in contact with the pubic symphysis. In some embodiments, the needle may be covered with a sheath to help with needle passage. In some embodiments, the handle assembly comprises a handle body, a handle insert, and an alignment bushing. In some embodiments, the handle insert is rotatably associated with both the handle body and the needle, and may be configured to rotate between a first or "unlocked" position in which the proximal end of the needle may be coupled (or uncoupled) with the handle assembly and a second or "locked" position in which the proximal end of the needle is secured to the handle assembly and the handle insert is securely mated with the handle body. In some embodiments, when the handle insert is in the locked position, the needle is prevented from moving relative to the handle assembly, enabling the user to guide the distal end of the needle by maneuvering the handle assembly. The implant delivery system of the present disclosure may be configured for use with a variety of surgical implants in any number of procedures. By way of example only, the implant delivery system is described herein within the context of implanting a retropubic midurethral sling to treat female urinary incontinence.

As additional description to the embodiments described below, the present disclosure describes the following embodiments.

Embodiment 1 is an implant delivery system for delivering a surgical implant to a surgical target site, comprising: (1) a handle body comprising a bulbous proximal end having a proximal recess formed therein, an elongated shaft extending distally from the bulbous proximal end along a longitudinal axis, the elongated shaft having a distal aperture, and an axial lumen extending through the elongated shaft along the longitudinal axis between the proximal recess and the distal aperture; (2) a handle insert having a proximal knob portion and an elongated shaft extending distally from the proximal knob portion, the elongated shaft having a needle coupling element at a distal end, the handle insert configured to reversibly couple with the handle body such that the elongated shaft is received within the axial lumen and the proximal knob portion is received within the proximal recess; and (3) a surgical needle having a proximal coupling element configured to removably couple with the handle insert, an implant coupling element configured to engage a surgical implant for delivery to a surgical target site, a generally cylindrical elongated shaft, and a shaped distal tip configured to penetrate patient anatomy; wherein the handle insert is configured to be coupled with the handle body in a first rotational orientation that enables coupling of the proximal coupling element of the surgical needle with the needle coupling element of the handle insert through the distal aperture of the handle body, and thereafter rotated to a second rotational orientation wherein the surgical needle is securely coupled with the handle insert and the handle insert is securely coupled with the handle body.

Embodiment 2 is the implant delivery system of embodiment 1, wherein the distal aperture comprises a tapered needle interface.

Embodiment 3 is the implant delivery system of embodiments 1 or 2, wherein the elongated shaft of the surgical needle has a curvilinear shape comprising a concave side and a convex side.

Embodiment 4 is the implant delivery system of any of embodiments 1 through 3, wherein at least one of the concave and convex sides comprises a rolled flat surface.

Embodiment 5 is the implant delivery system of any of embodiments 1 through 4, wherein the rolled flat surface has a curved component and a flat component.

Embodiment 6 is the implant delivery system of any of embodiments 1 through 5, wherein the curved component is oriented in the direction of the elongated shaft.

Embodiment 7 is the implant delivery system of any of embodiments 1 through 6, wherein the flat component is oriented in a direction transverse to the elongated shaft.

Embodiment 8 is the implant delivery system of any of embodiments 1 through 7, wherein the elongated shaft of the surgical needle includes an elongated flat surface extending substantially the length of the elongated shaft.

Embodiment 9 is the implant delivery system of any of embodiments 1 through 8, wherein the handle insert is nonthreadedly rotated within the handle body.

Embodiment 10 is the implant delivery system of any of embodiments 1 through 9, wherein the handle insert is rotated 90° in a clockwise direction to transition from the first rotational orientation to the second rotational orientation.

Embodiment 11 is the implant delivery system of any of embodiments 1 through 10, wherein the handle insert is configured to produce at least one of audible and tactile feedback upon completing a transition from the first rotational orientation to the second rotational orientation.

Embodiment 12 is the implant delivery system of any of embodiments 1 through 11, wherein the handle insert includes at least one deflectable member configured to forcibly deflect into a retention recess formed within the proximal recess upon completing a transition from the first rotational orientation to the second rotational orientation.

Embodiment 13 is the implant delivery system of any of embodiments 1 through 12, further comprising a protective sheath covering a substantial portion of the elongated shaft of the surgical needle, the surgical needle further comprising an unsheathed distal portion positioned between a distal end of the protective sheath and the shaped distal tip.

Embodiment 14 is the implant delivery system of any of embodiments 1 through 13, wherein the unsheathed portion comprises a visual depth indicator.

Embodiment 15 is the implant delivery system of any of embodiments 1 through 14, wherein the unsheathed portion has a length dimension within a range of 15 mm to 50 mm.

Embodiment 16 is the implant delivery system of any of embodiments 1 through 15, wherein the sheath has a color that provides contrast with patient anatomy under cytoscopy.

Embodiment 17 is the implant delivery system of any of embodiments 1 through 16, wherein the sheath is black.

Embodiment 18 is the implant delivery system of any of embodiments 1 through 17, wherein the sheath is a non-removable overwrap applied to the needle.

Embodiment 19 is an implant delivery system for delivering a surgical implant to a surgical target site, comprising: a handle member having an elongated shaft including a coupling element configured to removably couple with a surgical needle; a surgical needle having a proximal coupling element configured to removably couple with the handle element, an implant coupling element configured to engage a surgical implant for delivery to a surgical target site, a generally cylindrical elongated shaft, and a shaped distal tip configured to penetrate patient anatomy; wherein the elongated shaft of the surgical needle includes at least one elongated flat surface extending substantially the length thereof.

Embodiment 20 is the implant delivery system of embodiment 19, wherein the elongated shaft of the surgical needle has a curvilinear shape comprising a concave side and a convex side.

Embodiment 21 is the implant delivery system of embodiments 19 or 20, wherein the at least one elongated flat surface comprises a rolled flat surface on the concave side.

Embodiment 22 is a method for inserting a surgical needle into a patient along multiple trajectories, comprising: (1) providing a surgical needle having an elongated shaft, a shaped distal tip configured to penetrate patient anatomy, and a protective sheath covering a substantial portion of the elongated shaft, the surgical needle further comprising an unsheathed distal portion positioned between a distal end of the protective sheath and the shaped distal tip; (2) advancing the unsheathed distal portion of the surgical needle through a patient's skin such that the distal tip advances along a first trajectory within the patient; and (3) upon advancing the needle into the patient a distance equal to the length of the unsheathed distal portion, further advancing the distal tip into the patient along a second trajectory, the second trajectory being unequal to the first trajectory.

Embodiment 23 is the method of embodiment 22, wherein the unsheathed portion has a length dimension within a range of 15 mm to 50 mm.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIG. 6 is a perspective view of a handle body forming part of the implant delivery system of FIG. 1, according to some embodiments;

FIG. 7 is a top plan view of the handle body of FIG. 6, according to some embodiments;

FIG. 8 is a side plan view of the handle body of FIG. 6, according to some embodiments;

FIG. 13 is a perspective view of a handle insert forming part of the implant delivery system of FIG. 1, according to some embodiments;

FIG. 14 is an exploded perspective view of the handle insert of FIG. 13, according to some embodiments;

FIG. 15 is a perspective view of a knob forming part of the handle insert of FIG. 14, according to some embodiments;

FIG. 16 is another perspective view of the knob of FIG. 15, according to some embodiments;

FIG. 17 is a perspective view of an elongated shaft forming part of the handle insert of FIG. 13, according to some embodiments;

FIG. 18 is a side plan view of the elongated shaft of FIG. 17, according to some embodiments;

FIG. 19 is a perspective view of a needle forming part of the implant delivery system of FIG. 1, according to some embodiments;

FIG. 28 is a front plan view of the implant delivery system of FIG. 1 with the handle insert in an unlocked position, according to some embodiments;

FIG. 29 is a front plan view of the handle insert of FIG. 13 in an unlocked position coupled with the needle of FIG. 19, according to some embodiments;

FIG. 30 is a side plan view of the distal end of the handle insert of FIG. 13 in an unlocked position coupled with the needle of FIG. 19, according to some embodiments;

FIG. 31 is a front plan view of the implant delivery system of FIG. 1 with the handle insert in a locked position, according to some embodiments;

FIG. 32 is a front plan view of the handle insert of FIG. 13 in a locked position coupled with the needle of FIG. 19, according to some embodiments;

FIG. 33 is a front plan view of the distal end of the handle insert of FIG. 13 in a locked position coupled with the needle of FIG. 19, according to some embodiments;

FIGS. 36-45 are block diagrams of various steps of a method of using the implant delivery system of FIG. 1, according to some embodiments.

DETAILED DESCRIPTION OF A PREFERRED EMBODIMENT

Figure 1:
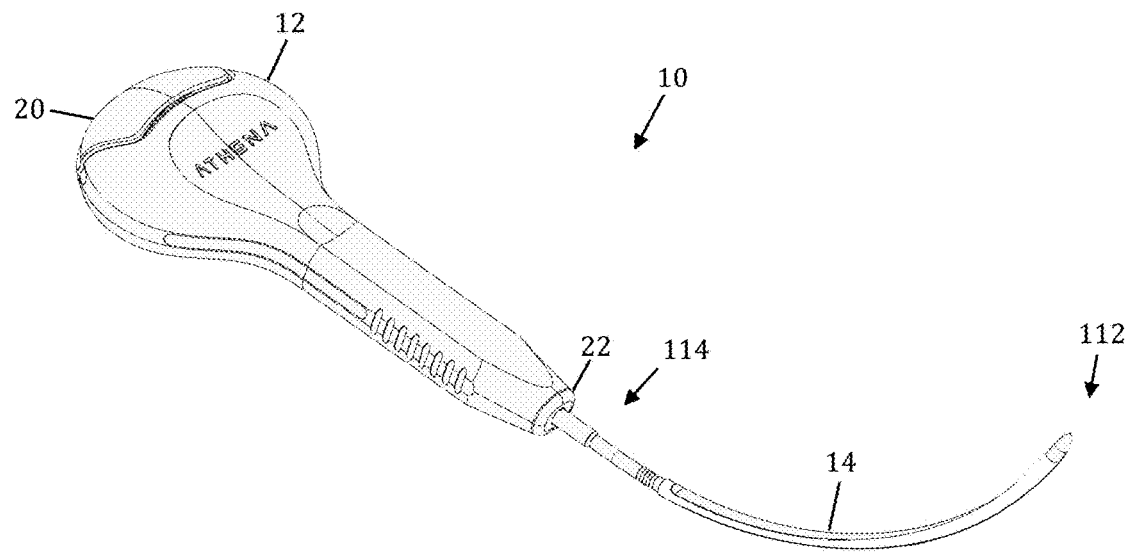
FIG. 1 is a perspective view of an implant delivery system according to some embodiments.
Figure 2:
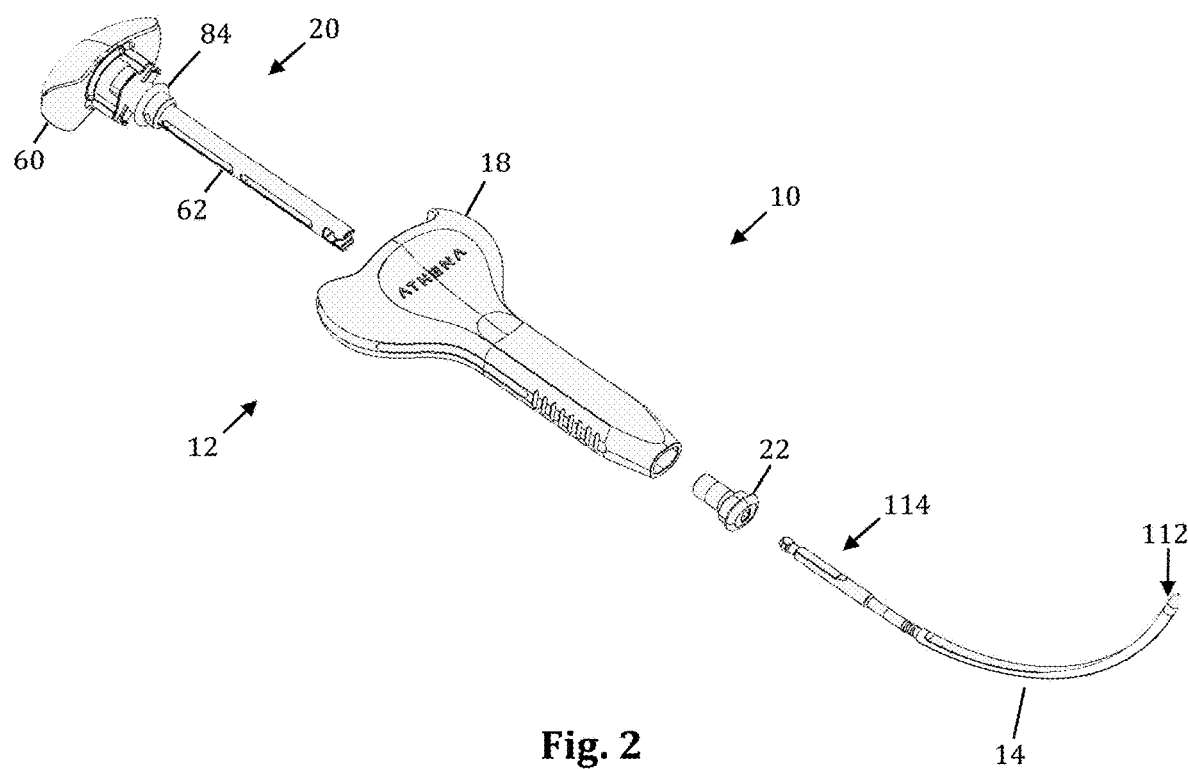
FIG. 2 is an exploded perspective view of the implant delivery system of FIG. 1, according to some embodiments.
Figure 3:
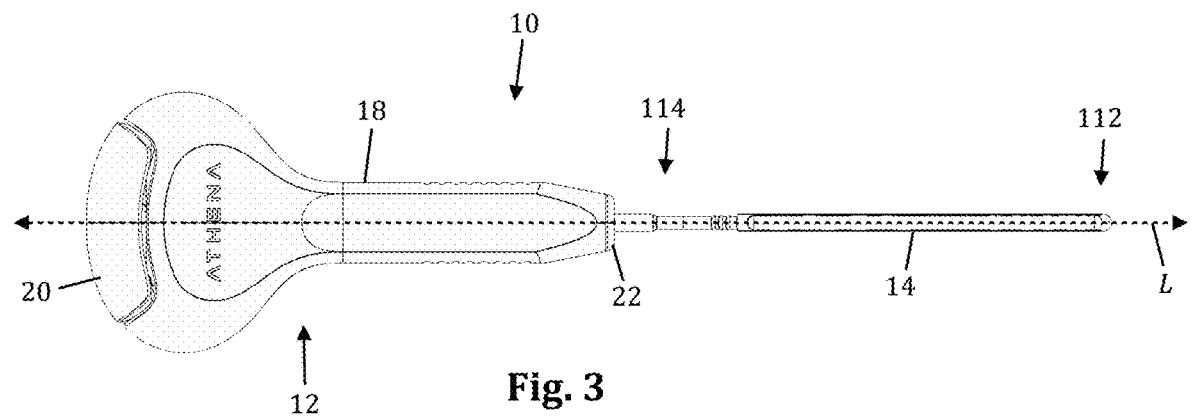
FIG. 3 is a top plan view of the implant delivery system of FIG. 1, according to some embodiments.
Figure 4:
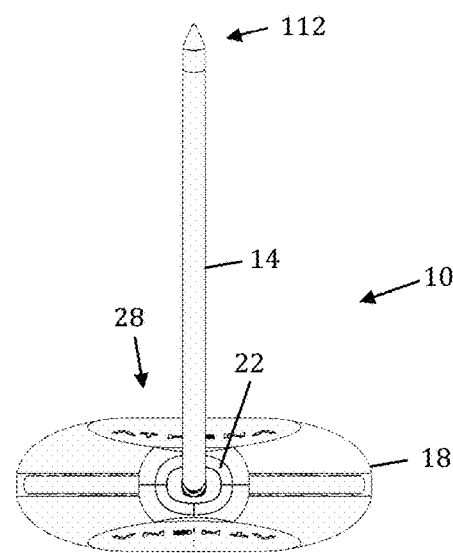
FIG. 4 is a distal end plan view of the implant delivery system of FIG. 1, according to some embodiments.
Figure 5:
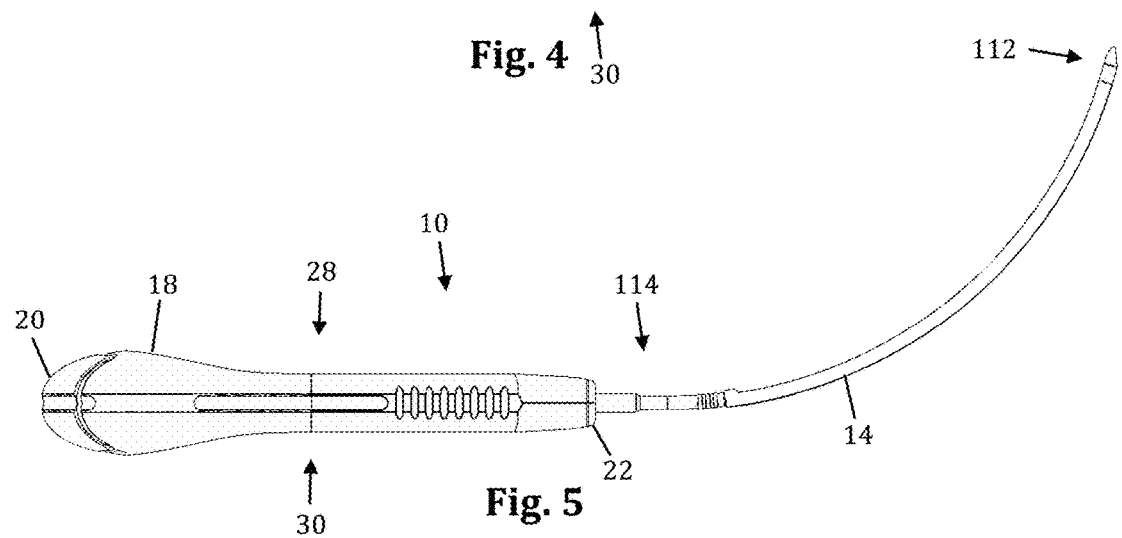
FIG. 5 is a side plan view of the implant delivery system of FIG. 1, according to some embodiments.
Figure 9:
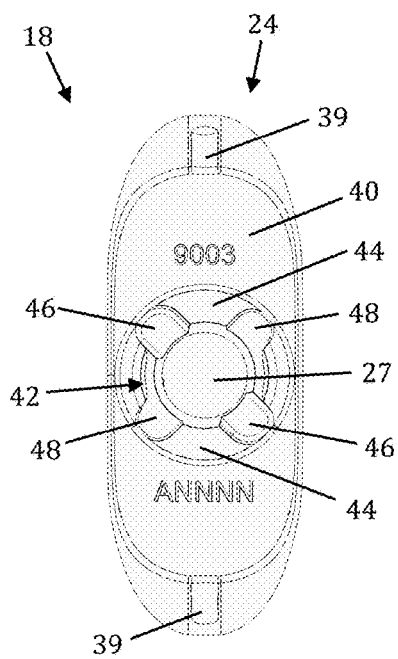
FIG. 9 is a proximal end plan view of the handle body of FIG. 6, according to some embodiments.
Figure 10:
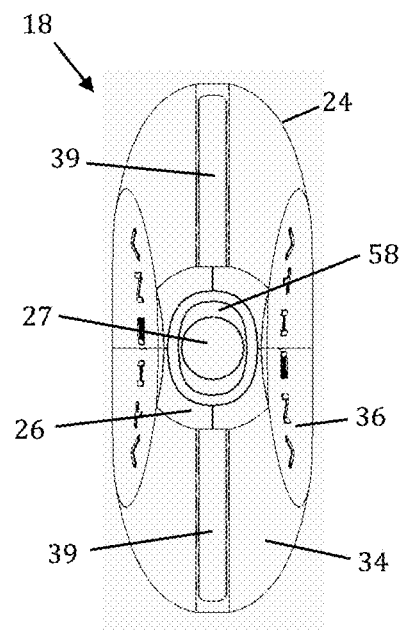
FIG. 10 is a distal end plan view of the handle body of FIG. 6, according to some embodiments.
Figure 11:
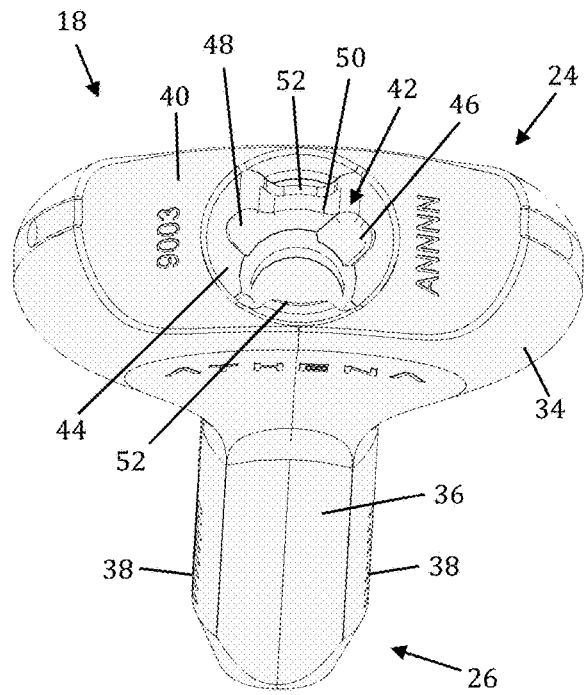
FIG. 11 is a perspective view of the proximal end of the handle body of FIG. 6, according to some embodiments.
Figure 12:
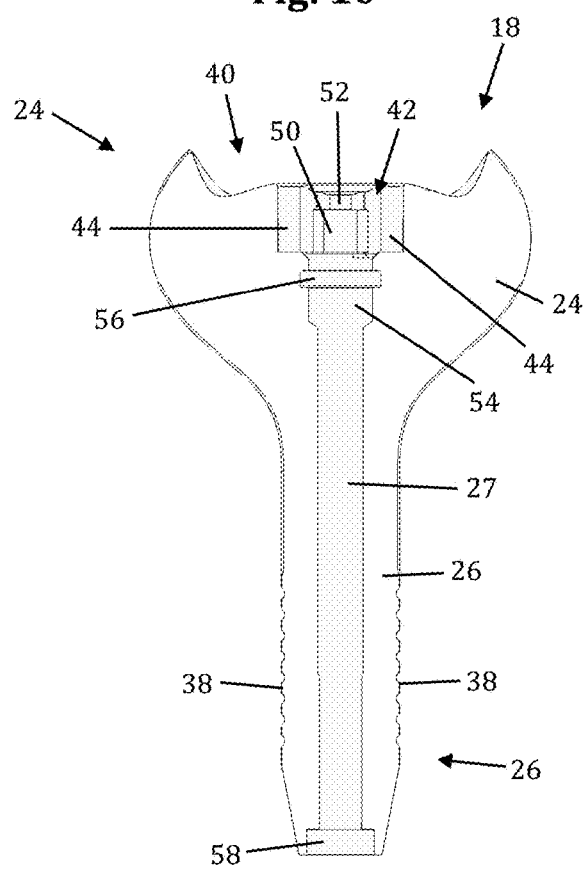
FIG. 12 is a sectional view of the handle body of FIG. 6, according to some embodiments.
Figure 20:
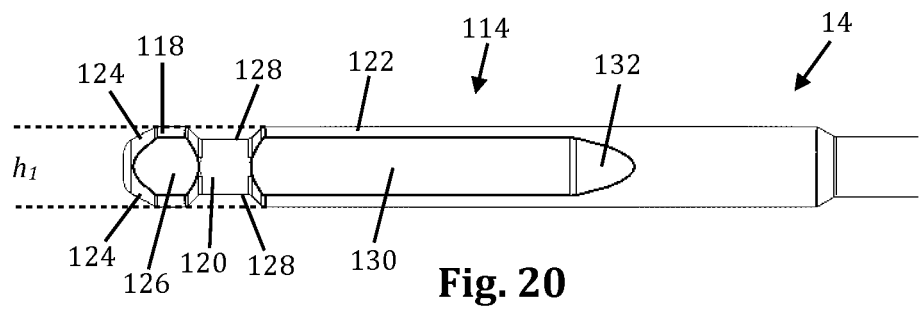
FIG. 20 is a top plan view of the proximal end of the needle of FIG. 19, according to some embodiments.
Figure 21:
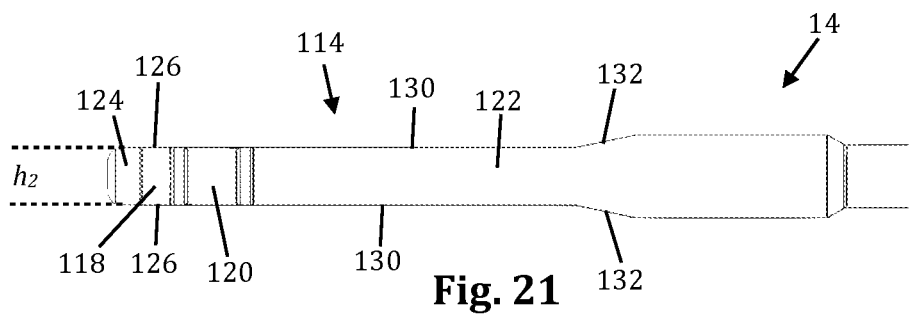
FIG. 21 is a side plan view of the proximal end of the needle of FIG. 19, according to some embodiments.
Figure 22A:
FIG. 22A is a perspective view of another needle forming part of the implant delivery system of FIG. 1, according to some embodiments.
Figure 22B:
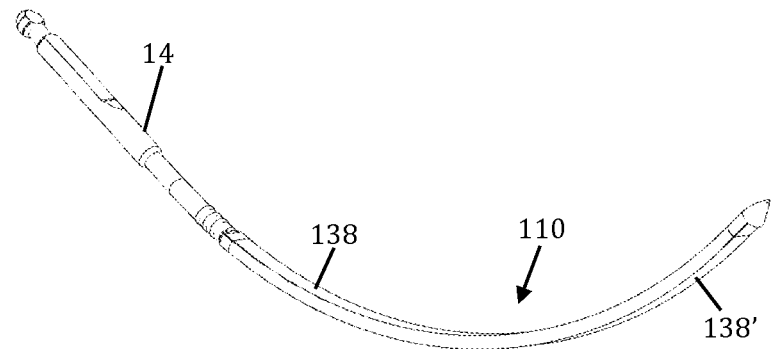
FIG. 22B is a perspective view of another needle forming part of the implant delivery system of FIG. 1, according to some embodiments.
Figure 23:
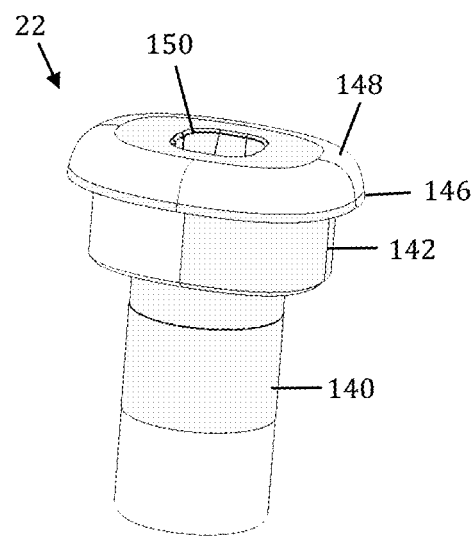
FIG. 23 is a perspective view of an alignment bushing forming part of the implant delivery system of FIG. 1, according to some embodiments.
Figure 24:
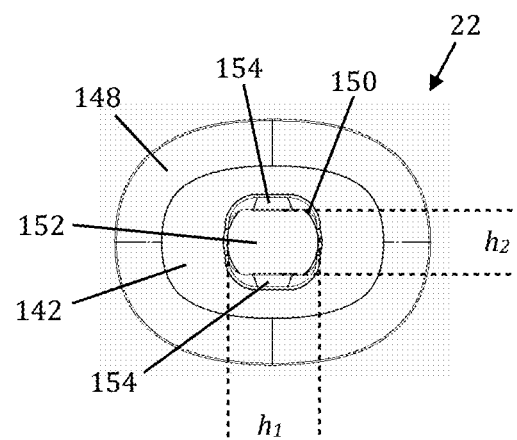
FIG. 24 is a plan view of the distal end of the alignment bushing of FIG. 23, according to some embodiments.
Figure 25:
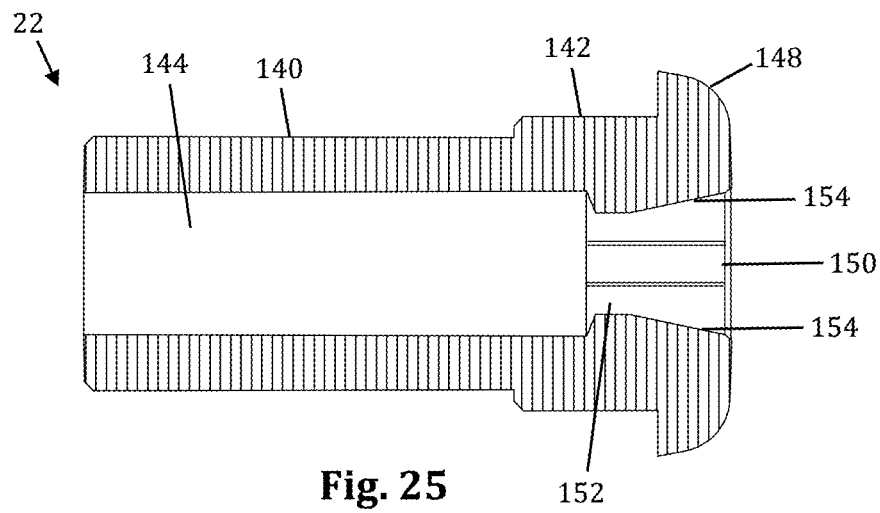
FIG. 25 is a sectional view of the alignment bushing of FIG. 23, according to some embodiments.
Figure 26:
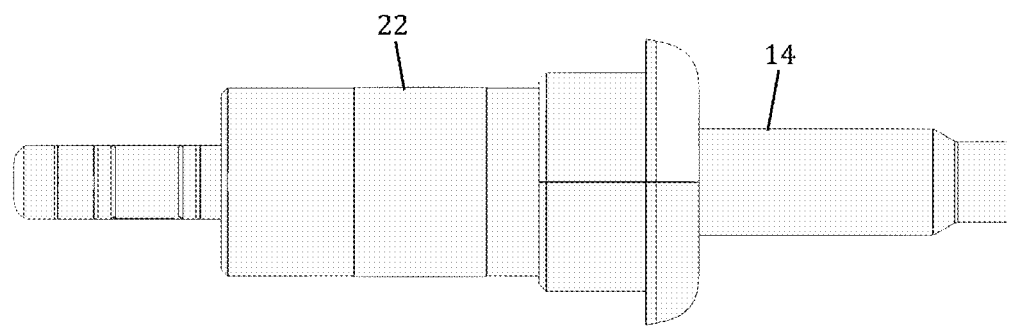
FIG. 26 is a side plan view of the alignment bushing of FIG. 23 coupled with the needle of FIG. 19, according to some embodiments.
Figure 27:
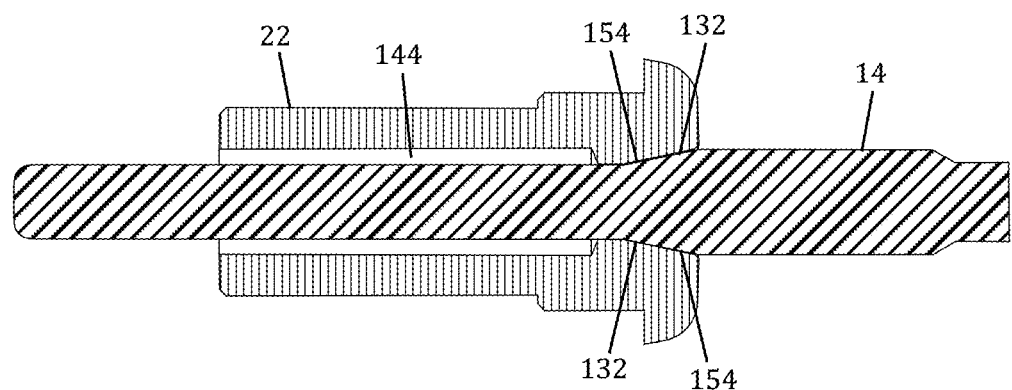
FIG. 27 is a sectional view of the alignment bushing and needle combination of FIG. 26, according to some embodiments.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The implant delivery system and related methods disclosed herein boasts a variety of inventive features and components that warrant patent protection, both individually and in combination.

FIGS. 1-5 illustrate one example of an implant delivery system 10 according to one embodiment of the present disclosure. By way of example only, the implant delivery system 10 may include a handle assembly 12 and a needle 14 removably engaged with the handle assembly 12. The needle 14 may be configured to engage with an implant 16 (e.g., see FIGS. 34-35), and is maneuverable by the handle assembly 12 to guide the implant 16 to a surgical target site within a patient. The handle assembly of the present example comprises a handle body 18, a handle insert 20, and an alignment bushing 22. The handle insert 20 is rotatably associated with both the handle body 18 and the needle 14, and is configured to rotate between a first or "unlocked" position in which the proximal end 114 of the needle 14 may be coupled with the handle assembly 12 and a second or "locked" position in which the proximal end 114 of the needle 14 is secured within the handle assembly 12 and the handle insert 20 is securely mated with the handle body 18. When the handle insert 20 is in the second position, the needle 14 is prevented from moving relative to the handle assembly 12, enabling the user to guide the distal end 112 of the needle 14 by maneuvering the handle assembly 12. The implant delivery system 10 of the present disclosure may be configured for use with a variety of surgical implants in any number of procedures. By way of example only, the implant delivery system 10 is described herein in conjunction with implanting a retropubic midurethral sling to treat female incontinence.

FIGS. 6-12 illustrate an example of a handle body 18 according to one embodiment of the present disclosure. By way of example, the handle body 18 has a general bulbous or "tear drop" shape and includes a proximal "bulb" portion 24, a distal "stem" portion 26, and axial lumen 27 extending longitudinally through the handle body 18 from the proximal bulb portion 24 to the distal stem portion 26. The handle body 18 further includes a first or front face 28, a second or back face 30, and a pair of opposing lateral sides 32. The distal stem portion 26 comprises an elongated shaft extending linearly from the proximal bulb portion 24 along longitudinal axis L. It should be noted that the handle body 18 has multiple planes of symmetry, e.g., the first and second faces 28, 30 are symmetrical to one another about the frontal plane F, and the pair of opposing lateral sides 32 are symmetrical to one another about the medial plane M, and that symmetry (or a mirrored symmetry) exists in all internal structure as well. The left-right or medial symmetry is important to ensure ambidextrous use. The addition of top-bottom or frontal symmetry ensures the needle 14 and handle insert 20 may be coupled with the handle body 18 in any orientation allowed by the structure, and directionality (e.g., "front" and "back") is not assigned or apparent until the needle 14 is secured to the handle assembly 12 (as described below) in which case the "front" face 28 is the face of the handle body 18 coinciding with the curvature direction of the needle 14 (see, e.g., FIGS. 4-5). In embodiments or procedures in which a straight needle is used, the handle assembly 12 would not have a specific directionality.

The handle body 18 has a shape configured to enable a user to control the handle body 18 (and thus the implant delivery system 10) with one hand, leaving the other hand free to perform additional tasks while maintaining the handle body 18 in a horizontal plane throughout the procedure, and allowing the user to detect and correct needle canting. By way of example only, the handle body 18 has a length dimension l that is suitable for ergonomic association with a user's hand in multiple grip configurations. The proximal bulb portion 24 has a width dimension $w_2$ that is greater than the width dimension $w_1$ of the distal stem portion 26, and a thickness dimension 12 that is greater than the thickness dimension $t_1$ of the distal stem portion 26. The handle body 18 further comprises a generally convex outer surface 34 encompassing at least a portion of the front and back faces 28, 30, and the opposing sides 32. Each of the front and back faces 28, 30 may include a generally concave surface 36 formed therein to improve the ergonomic feel of the handle body 18 (for example by conforming to a user's hand when holding the handle body 18). In some embodiments, the generally concave surface 36 is formed symmetrically about a longitudinal midline of the handle body 18. The sides 32 of the distal stem portion 26 are generally flat and may include a friction element 38 (e.g., a plurality of ridges, recesses, bumps, and the like) configured to provide a textured grip for the user's fingers, and an alignment line 39 configured to enhance the visibility of the flat sides 32 to assist the surgeon user in maintaining the horizontal plane and resist canting of the needle 14. By way of example, the alignment line 39 may be any treatment that provides visual distinction, including but not limited to color differential, etching, or a surface structure such as an elongated concave recess as shown.

In addition to providing a superior ergonomic feel, the tear drop shape and other features of the handle body 18 function to maximize the safety and effectiveness of the procedure by increasing tactile response and surgeon repeatability and reproducibility by providing visual features that the surgeon may associate with anatomical landmarks to maintain horizontal plane alignment of the handle body 18 throughout the procedure, thus reducing or eliminating needle 14 canting while the needle 14 is advanced through the patient anatomy and maneuvered around the pubic bone. For example, during initial horizontal needle 14 insertion, the bulb portion 24 is configured to rest above the crook of the user's thumb while the user's fingers engage the friction elements 38 of the flat sides 32. The flat sides 32 enable the user to tactically maintain horizontal plane alignment during this part of the procedure, and the alignment lines 39 on each side 32 of the handle body 18 enable the user to visually maintain horizontal plane alignment. When it is time to maneuver the needle vertically around the pubic bone, the user may change hand orientation such that the bulb portion 24 is placed in the user's palm and the stem 26 extends though space between the user's fingers.

Referring now to FIGS. 9-12, the proximal bulb portion 24 may have a proximally-facing cutaway portion 40 sized and configured to receive the head 64 of the knob 60 of the handle insert 20 therein. When the knob head 64 is rotated into a locked position, the knob head 64 may fill the cutaway portion 40 such that the outer perimeter of the handle assembly 12 is "completed" (e.g., as shown in FIGS. 1-5). The proximal bulb portion 24 may further include a generally cylindrical recess 42 formed within the cutaway portion 40 along longitudinal axis L, and positioned between the cutaway portion 40 and the axial lumen 27. The recess 42 is sized and configured to rotatably receive the neck portion 66 of the knob 60 of the handle insert 20 therein. The recess 42 further comprises a pair of opposing rotation tracks 44 each configured to enable partial orbital translation (e.g., by way of approximately 90° rotation of the knob 60) of the deflectable tabs 78 of the knob post 68 of the handle insert 20 within the rotation tracks 44. Each rotation track 44 includes a first detent (e.g., recess) 46 at one end and a second detent (e.g., recess) 48 at the other end. By way of example only, the first detents 46 are configured to receive the distal protrusions 80 of the deflectable tabs 78 when the handle insert is in an "unlocked" position, and the second detents 48 are configured to receive the distal protrusions 80 of the deflectable tabs 78 when the handle insert 20 is rotated into the "locked" position. In some embodiments, the first detents 46 may be formed with a greater depth than the second detents 48 which, in combination with a flexible retaining element (e.g., canted coil spring) 84, may help to bias the handle insert 20 into the unlocked position. By way of example, the recess 42 may include an axial protrusion 50 positioned between the first detent 46 of one rotation track 44 and the second detent 48 of the other rotation track 44, the axial protrusion 50 configured to prevent over-rotation of the handle insert 20 by presenting a physical barrier to further rotation of longitudinal flanges 74 of the knob neck 66 and/or the deflectable tabs 78 of the knob post 68 (e.g., to ensure the needle 14 is secured to the handle assembly 16). The recess 42 of the present example may further include an overhang 52 or other trapping element configured to prevent ejection of the handle insert 20 from the recess 42 during rotation, for example by presenting a physical barrier that interacts with transverse flanges 76 on the knob neck 66 to prevent proximal translation of the handle insert 20 during rotational movement.

The proximal bulb portion 24 further comprises the proximal end 54 of the axial lumen 27. By way of example only, the proximal end 54 is sized and configured to receive the knob post 68 therein, and thus may have a diameter that is greater than the diameter of the main portion of the axial lumen 27. The proximal end 54 may further include a circumferential recess 56 sized and configured to receive at least a portion of the flexible retaining element (e.g., canted coil spring) 84 therein. The proximal end 54 of the axial lumen 27 opens into the recess 42 to provide access to the axial lumen 27, for example by the handle insert shaft 62 described below.

The main portion of the axial lumen 27 may comprise an elongated cylindrical passage extending axially through the distal stem portion 26. By way of example only, the axial lumen 27 is sized and configured to rotatably receive the elongated shaft 62 of the handle insert 20 therein. The distal stem portion 26 may include a distal recess 58 surrounding the distal opening of the axial lumen 27. By way of example, the distal recess 58 has a perimeter shape complimentary to the shape of the distal portion 142 of the alignment bushing 22. By way of example, the perimeter shape may be any shape that prevents rotation of the alignment bushing 22 within the distal recess 58, including but not limited to elliptical, oval, or polygonal.

FIGS. 13-18 illustrate an example of a handle insert 20 according to one embodiment of the disclosure. By way of example, the handle insert 20 of the present embodiment comprises a knob 60 and an elongated shaft 62 extending distally from the knob 60. The knob 60 may include a proximal head 64, a neck 66 positioned distally of the head 64, and a post 68 extending distally from the neck 66. By way of example, the head 64 may have a smooth arcuate proximal surface 70 and a distal facing surface 72, and is configured to nest within the cutaway portion 40 of the handle body 18 when in the locked position. The head 64 functions as a rotation handle in that the user will apply torque to the head 64 to rotate the handle insert 20 and secure the needle 14 to the handle assembly 12. In some embodiments, the head 64 may further include an alignment line 71 provided on the proximal surface 70 and congruent with the alignment line(s) 39 on the flat sides 32 of the handle body 18, to assist the surgeon user in maintaining the horizontal plane and resist canting of the needle 14. By way of example, the alignment line 71 may be any treatment that provides visual distinction, including but not limited to color differential, etching, or a surface structure such as an elongated concave recess as shown.

The neck 66 extends distally from the head 64, is generally cylindrical in shape, and is configured to mate with the recess 42 of the handle body 18 as described above. The neck 66 may include one or more rotation stops (e.g., longitudinal flanges 74) that interact with a corresponding feature of the recess 42 (e.g., axial protrusions 50) to prevent over-rotation of the handle insert 20 within the handle body 20. The neck 66 may also include an anti-displacement feature (e.g., transverse flange 76) configured to interact with a corresponding feature of the recess 42 (e.g., overhang 52) to prevent proximal translation of the handle insert 20 during rotation.

By way of example, the post 68 is generally cylindrical in shape and extends distally from the neck 66. At least a portion of the post 68 is sized and configured to nest within the proximal end 54 of the axial lumen 27. The post 68 may further include a locking element configured to secure the handle insert 20 in both the unlocked and locked positions. By way of example only, the locking element may be a pair of opposing deflectable tabs 78 extending transversely from the proximal portion of the post 68. The deflectable tabs 78 are sized and configured to orbitally translate within the rotation track 44 of the handle body 18. The deflectable tabs 78 each have a distal protrusion 80 configured to nest in the first and second detents 46, 48 of the handle body 18. More specifically, the distal protrusions 80 of the deflectable tabs 78 nest within the first detents 46 when the handle insert is in an initial "unlocked" position. To rotate the handle insert 20 from the unlocked position to the locked position, a user applies sufficient torque on the knob head 64 in a clockwise direction to force the distal protrusions 80 out of the first detents 46 while deflecting the deflectable tabs 78 proximally. The deflectable tabs 78 then orbitally translate along the rotation track 44 until the distal protrusions 80 enter the second detents 48, at which point the deflection tabs 78 "snap" back to near original position, "locking" the distal protrusions 80 within the second detents 48 while simultaneously giving the user audible and tactile confirmation of a successful lock.

The post 68 further includes a circumferential recess 82 configured to receive at least a portion of the flexible retaining element (e.g., canted coil spring) 84 therein. Upon mating of the handle insert 20 with the handle body 18, the circumferential recess 82 is aligned with the circumferential recess 56 of the handle body 18 to trap the canted coil spring 84 therein. By way of example, this acts as to secure the handle insert 20 to the handle body 18 while in the unlocked position. The distal end of the post 68 includes an axial recess 86 configured to receive the elongated shaft 62 therein, which is secured to the knob 60 by way of a retaining pin 88 extending through transverse apertures 90 on the post 68 and pin apertures 92 on the elongated shaft 62. In some embodiments, the flexible retaining element 84 may be initially provided or mounted within the circumferential recess 56 of the handle body 18. In some embodiments, the flexible retaining element 84 may be initially provided or mounted within the circumferential recess 82 of the handle insert 20.

By way of example only, the elongated shaft 62 is generally cylindrical in shape, and is sized and configured to slidingly nest within the axial lumen 27 of the handle body 18. The elongated shaft 62 has a proximal end 94 and a distal end 96. The proximal end 94 is sized and configured to mate with the axial recess 86 of the knob 60 described above, and includes pin apertures 92 for receiving the retaining pin 88 to secure the elongated shaft 62 to the knob 60. The distal end 96 includes a capture element configured to enable ingress and/or egress of the proximal end 114 of the needle 14 while the handle insert 20 is in the unlocked position (See, e.g., FIGS. 28-30), and is further configured to capture (e.g., prevent egress of) the proximal end 114 of the needle 14 when the handle insert 20 is in the locked position, thereby securely coupling the needle 14 to the handle assembly 12 (See, e.g., FIGS. 31-33). By way of example only, the capture element of the present embodiment may comprise a chamber 98 formed between opposing distal flanges 100 extending axially from the distal end 96 of the shaft 62. The chamber 98 is sized and configured to receive the proximal knob 118 of the needle 14 therein, and is defined by a distance $d_1$ between the opposing distal flanges 100. The flanges 100 each have an inner-facing transverse ridge 102 or other suitable blocking element configured to interact with the proximal end 114 of the needle 14 (e.g., the neck 120) to capture the proximal knob 118 of the needle 14 within the chamber 98 when the handle insert 20 is in the locked position. The distance $d_2$ between the opposing transverse ridges 102 defines a gap 104 through which the proximal knob 118 of the needle 14 must pass to enter or exit the chamber 98 during coupling and uncoupling of the needle 14 and handle assembly 12. By way of example, the distance $d_2$ is less than the distance $d_1$. In some embodiments, each of the transverse ridges 102 has a sloped distal surface 106 to help guide the proximal knob 118 into the gap 104 during coupling of the needle 14 to the handle assembly 12.

FIGS. 19-22B illustrate an example of a needle 14 according to one embodiment of the disclosure. By way of example, the needle 14 may comprise a rigid elongated curvilinear shaft 110 extending between a distal end 112 and a proximal end 114. In some embodiments, the elongated shaft 110 may have a curvilinear longitudinal axis and a generally cylindrical shape extending along the axis, and may preferably include an elongated rolled flat or arcuate surface 138, for example the inside or concave surface of the curvilinear shaft 110. By way of example, the rolled flat surface 138 has an arcuate component in the direction of the curvilinear longitudinal axis of the needle 14, and a flat component in the direction transverse to the longitudinal axis. Optionally, in any embodiment, the elongated shaft 110 may have a fully cylindrical shape without a rolled flat surface, as shown by way of example only in FIG. 22A. Optionally, in any embodiment, the elongated shaft 110 may have opposing rolled flat surfaces such that the inside or concave surface may have a rolled flat surface 138 and the outside or convex surface may comprise a rolled flat surface 138', as shown by way of example only in FIG. 22B. In some embodiments, the shaft 110 may be curved along a single plane (e.g., medial plane) such that when the proximal end 114 is horizontally oriented, the distal end 112 is vertically oriented (or near-vertically oriented). In some embodiments, the elongated shaft 110 may be straight. The distal end 112 comprises a shaped end or tip 116 configured to enable the needle 14 to pass through patient tissue with minimal disruption. By way of example, the shaped end 116 may be generally conical, pointed, tapered, and the like.

By way of example, when used in a RMUS procedure as described herein, the rolled flat surface 138 comprises an anterior (or anterior-facing) surface as it is oriented toward the anterior aspect of the patient. In some embodiments, the rolled flat surface 138 on a curved needle may provide the user with tactile and/or visual confirmation of needle orientation during insertion into the patient's body, which may improve the repeatability and reproducibility of the given procedure. For example, the rolled flat surface 138 may give the surgeon user the ability to see the orientation of the needle during insertion, increasing the ability to maintain the horizontal plane and prevent canting during insertion. Similarly, placing a finger on the rolled flat surface 138 may provide the surgeon user with tactile confirmation of the needle orientation. Furthermore, the rolled flat surface 138 may improve orientation and tracking when in contact with patient anatomy (e.g., pubic symphysis in the case of a RMUS procedure). A second rolled flat surface 138 on the outer/convex/posterior side of the needle 14 may reduce the profile of the needle 14 enabling an easier passage through the patient anatomy with minimal disruption, including increased avoidance of bladder perforation.

The proximal end 114 includes a locking element configured to interact with the distal end 96 of the elongated shaft 62 of the handle insert 20 to securely lock the needle 14 to the handle assembly 12. In some embodiments, the proximal end 114 comprises a proximal knob 118, a neck 120 extending distally from the proximal knob 118, and a shoulder portion 122 extending proximally of the neck 120. The proximal end 114 may be configured for insertion through the gap 104 into the chamber 98 of the distal end 96 of the shaft 62 when the handle insert 20 is in the unlocked position, and then captured within the chamber 98 when the handle insert 20 is rotated into the locked position. By way of example only, the proximal knob 118 has a maximum height dimension $h_1$ that corresponds to the distance $d_1$ defining the chamber 98. The proximal knob 118 may further comprise a pair of proximal tapered surfaces 124 configured to help guide the proximal knob 118 into the gap 104 during coupling of the needle 14 to the handle assembly 12. Notably, the proximal knob 118 may include a pair of opposing planar surfaces 126 formed parallel to the frontal plane F and having a distance between them defining a minimum height dimension $h_2$ (where $h_2 < h_1$) corresponding to the distance $d_2$ of the gap 104, enabling passage of the proximal knob 118 through the gap 104 when the handle insert 20 is in the unlocked position.

When the proximal knob 118 is positioned within the chamber 98 of the handle insert 20, the neck 120 is aligned within the gap 104 (e.g., see FIG. 30). By way of example only, the neck 120 may be generally cylindrical in shape, and has a diameter that is equal to the distance $h_2$ between the opposing planar surfaces 126 of the proximal knob 118 (and also the opposing planar surfaces 130 of the shoulder portion 122). For example, in one orientation (e.g., the view of FIG. 22) the neck 120 comprises a pair of recesses 128 formed by the height differential between the neck 120 and maximum height dimensions of the proximal knob 118 and shoulder 122. The recesses 128 are sized and configured to securely receive the blocking elements (e.g., transverse ridges 102) of the handle insert 20 as the handle insert 20 is rotated into the locked position, thus preventing the proximal knob 128 from exiting the chamber 98 (e.g., see FIG. 33).

By way of example only, the shoulder portion 122 is distally adjacent to the neck 120 and has a maximum height dimension $h_1$ that is identical or substantially similar to the maximum height dimension $h_1$ of the proximal knob 118 and also the width dimension of the alignment aperture 152 of the alignment bushing 22. Similar to the proximal knob 118, the shoulder portion 122 includes a pair of opposing planar surfaces 130 formed parallel to the frontal plane/and having a distance between them defining a minimum height dimension $h_2$ (where $h_2 < h_1$) corresponding to the height of the alignment aperture 152 of the alignment bushing 22, enabling passage of the shoulder 122 (and proximal knob 118) through the alignment aperture 152 of the alignment bushing 22 while preventing rotation and/or canting of the needle 14. The distal portion of the shoulder 122 may include tapered surfaces 132 to transition between the planar surfaces 130 and the full diameter of the needle 14.

In some embodiments, the needle 14 may further include an implant attachment element or assembly point 133, for example a circumferential recess 134 with a friction element 136 configured to hold the implant 16 (e.g., sling) in place during deployment of the needle to deliver the implant 16 to the surgical target site. (See, e.g., FIG. 35).

FIGS. 23-27 illustrate an example of alignment bushing 22 according to one embodiment of the disclosure. By way of example only, the alignment bushing 22 of the present embodiment includes a proximal portion 140, a distal portion 142, and an inner lumen 142 extending axially therethrough. The proximal portion 140 is sized and configured for mating with the axial lumen 27 of the handle body 18. The distal portion 142 is sized and configured to nest within the distal recess 58 of the handle body 18. By way of example, the distal portion 142 has a perimeter shape complimentary to the shape of the distal recess 58 of the alignment bushing 22. By way of example, the perimeter shape may be any shape that prevents rotation of the alignment bushing 22 within the distal recess 58, including but not limited to elliptical, oval, or polygonal. The distal portion 142 further comprises a lip 146 having a curved outer surface 148 that provides a smooth edge surface for the distal end of the handle assembly 12, to minimize the risk of trauma to the patient tissue during the procedure.

By way of example, the distal portion 142 further comprises a distal aperture 150, an alignment aperture 152 positioned proximally of the distal aperture 150, and a pair of tapered surfaces 154 extending between the distal aperture 150 and the alignment aperture 152. The alignment aperture has a first size dimension (e.g., width) corresponding to the maximum height dimension $h_1$ of the proximal knob 118 and shoulder 122 of the needle 14, and a second size dimension (e.g., height) corresponding to the minimum height dimension $h_2$ of the proximal knob 118 and shoulder 122 of the needle 14. This size configuration ensures that the needle 14 is properly oriented relative to the handle assembly 12 upon coupling the needle 14 to the handle assembly 12 and further upon locking the needle 14 to the handle assembly 12. The tapered surfaces 154 help to guide the proximal knob 118 of the needle 14 through the alignment aperture 152 and are configured to flushly mate with tapered surfaces 132 of the needle 14 (e.g., see FIG. 27) to limit the advancement of the needle 14 into the alignment bushing 22 and handle body 18, ensuring that the proximal knob 118 is properly positioned for capture by the handle insert 20.

Figure 34:
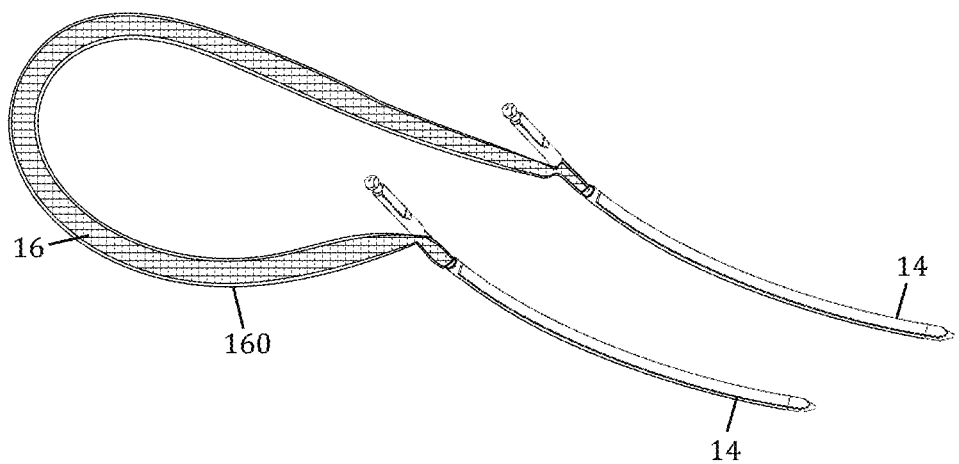
FIG. 34 is a perspective view of an implant delivery system of FIG. 1 alongside an implant according to some embodiments.
Figure 35:
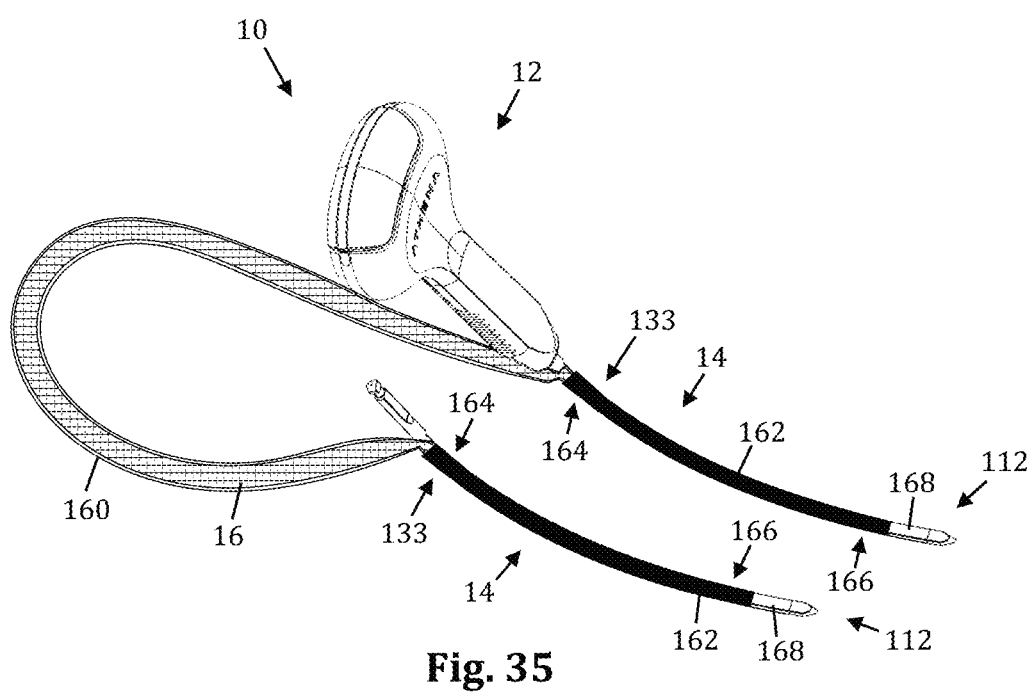
FIG. 35 is a perspective view of an implant delivery system of FIG. 1 coupled with an implant, according to some embodiments.

Referring to FIGS. 34-35, the implant 16 of the present example embodiment comprises a flexible urethral sling, for example made of polypropylene mesh. In some embodiments, the sling 16 may have looped edges that resist roping and provide tissue engagement without fraying. In some embodiments, a sling sheath 160 (e.g., made of plastic or other suitable material) may be provided to cover the sling 16 to reduce friction with patient anatomy during insertion. FIG. 34 depicts an example of a flexible urethral sling 16 covered with an elongated sheath 160 and coupled to a needle 14 at each end, as used in a RMUS procedure (such as the one described by way of example only below). By way of example, the flexible urethra sling 16 and sheath 160 attach to the needles 14 at assembly points 133.

In some embodiments, the needle 14 may be covered or wrapped with a needle sheath 162, which may be applied by heat shrinking (for example). In some embodiments, the sheath 162 is non-removable. The needle sheath 162 functions to reduce friction of the needle during insertion and also to increase visualization of the needle during cytoscopy, both of which may reduce the occurrence of bladder perforation. Bladder perforation may not be a major complication of the procedure if recognized during the cytoscopy phase of needle placement. Improved visibility of the needle 14 during cytoscopy may increase a physician's ability to avoid perforation of the bladder during use. By way of example only, the needle sheath 162 may preferably be black in color for best visualization during cytoscopy, however any color may be used that provides sufficient contrast with the bladder under cytoscopy. By way of example, the proximal end 164 of the needle sheath 162 may be configured to cover the assembly point 133 of the needle 14 and implant 16.

In some embodiments, the distal end 166 of the needle sheath 16 may not extend to the distal end 112 of the needle 14, but rather is positioned to end a predetermined distance from the shaped end 116 to create an exposed portion 168 of the needle 14. The exposed portion 168 may be used as depth indicator or point of reference, for example to visually indicate to the surgeon when the needle 14 has penetrated a sufficient distance into the patient tissue in one direction before maneuvering the handle assembly 12 to orient the needle 14 in a different direction. For example in a RMUS procedure, the curved needle 14 is inserted behind the pubic symphysis. This requires inserting the needle 14 at one angle, and then maneuvering the handle assembly 12 to cause the shaped end 116 of the needle 14 to traverse the tissue in a different direction (e.g., around the pubic symphysis). In such a procedure, when the surgeon user sees that the exposed portion 168 has been fully inserted, the surgeon would know that the needle 14 has been inserted to a sufficient depth to begin maneuvering the handle assembly 12 to change the insertion trajectory of the needle tip. In some embodiments, the exposed portion 168 may also be grasped with a forceps (e.g., during needle removal) to avoid damaging the sheath 162.

In some embodiments, the exposed portion may have a length dimension in the range of 10-50 mm. As such, the length of the exposed portion can be about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, or any amount or range therein in increments of 0.1 mm As previously mentioned, the implant delivery system 10 may be used in any suitable procedure without reservation. By way of example only, the implant delivery system 10 is described herein for use in a retropubic mid-urethral sling procedure to treat female urinary incontinence.

Before the patient is prepped and draped, she should be placed in the lithotomy position, taking care to avoid hip flexion greater than 60°. The user (e.g., surgeon) may the insert a catheter (e.g., an 18 French Foley catheter) into the bladder and leave it to open to drainage. The two needle exit sites 170 are then located and marked on the patient's skin, for example approximately 2-2.5 cm on each side of the midline, immediately above the pubic symphysis and in contact with the dorsal aspect of the pubic bone 172, as shown by way of example in FIG. 36. To avoid the inferior epigastric vessels, it is important that the intended exit sites 170 are not more than 2.5 cm from the midline. The exit sites 170 must be near midline and close to the superior aspect of the pubic bone to avoid anatomic structures in the abdomen, inguinal area and lateral pelvic sidewall. At the level of the mid urethra, a small amount of local anesthesia may then be injected submucosally to create a space between the vaginal wall and the periurethral fascia. A retropubic hydrodissection may be performed using two injections of normal saline on either side of midline. Starting at the exit sites 170, a needle (e.g., 18 gauge) may be passed along the back of the pubic bone until the tip of the needle touches the endopelvic fascia. The needle may then be slowly withdrawn while injecting 30 to 50 cc of saline to open the retropubic space to minimize the risk of bladder 174 puncture during the implant placement. Two forceps may then be used to grasp the vaginal wall at each side of the urethra. A sagittal incision no more than 1.5 cm long may be made with a small scalpel starting approximately 1.0 cm cephalad from the urethral meatus. This incision will be positioned over the mid-urethral zone and will allow for subsequent implant passage. Two small paraurethral lateral dissections (approximately 0.5 to 1.0 cm) may be made with a small pair of blunt scissors between the vaginal wall and periurethral fascia to accommodate insertion of the needle tips 116. The bladder 174 may then be drained via catheter 176 and confirmed empty. A rigid catheter guide may be inserted into the channel of the catheter to allow contralateral displacement of the bladder, bladder neck and urethra away from the tip 116 of the needle 14 as it passes through the retropubic space, as shown by way of example in FIGS. 37A-37B.

At this point, the patient is prepared for insertion of the implant 16 (e.g., elongated mesh sling coupled to a needle 14 at each end) using the implant delivery system 10 of the present disclosure. As a first step, a handle insert 20 is inserted into a handle body 18 and positioned in an unlocked position (e.g., fully rotated counter clockwise such that the knob 60 is perpendicular to the frontal plane (e.g., front and back faces 28, 30) of the handle body 18, as shown by way of example in FIG. 28). The implant 16 is then coupled to the handle assembly 12 by inserting the proximal end 114 of one of the needles 14 coupled to the implant 16 into the handle body 18 as described above. The needle 14 is secured in position by rotating the knob 60 clockwise until aligned with the shape of the handle body 18, as shown by way of example in FIG. 31. The user may also experience audial and/or tactile confirmation of successful locking as described above. The user may then confirm that the needle 14 is properly secured to the handle assembly 12 by applying tension between the mated components.

Figure 38:
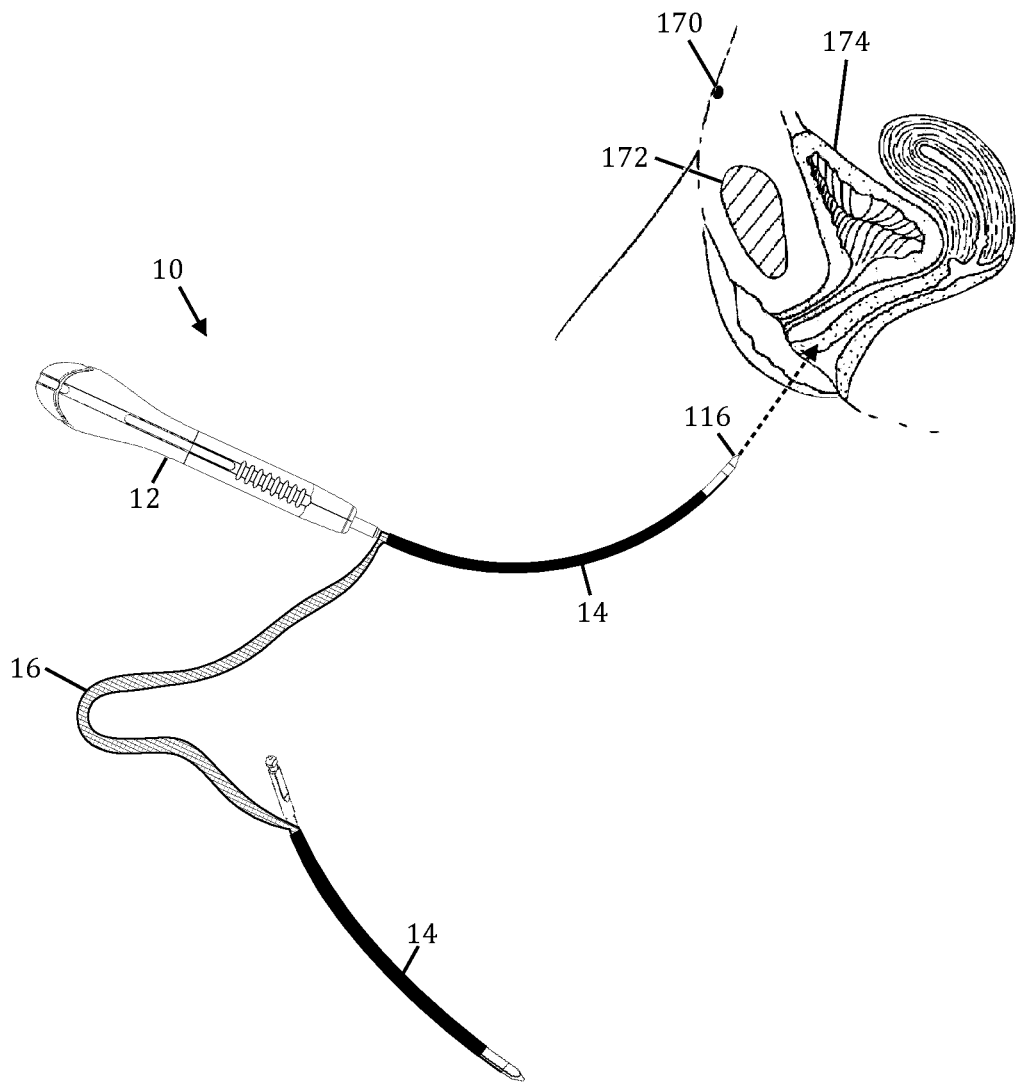
Figure 39:
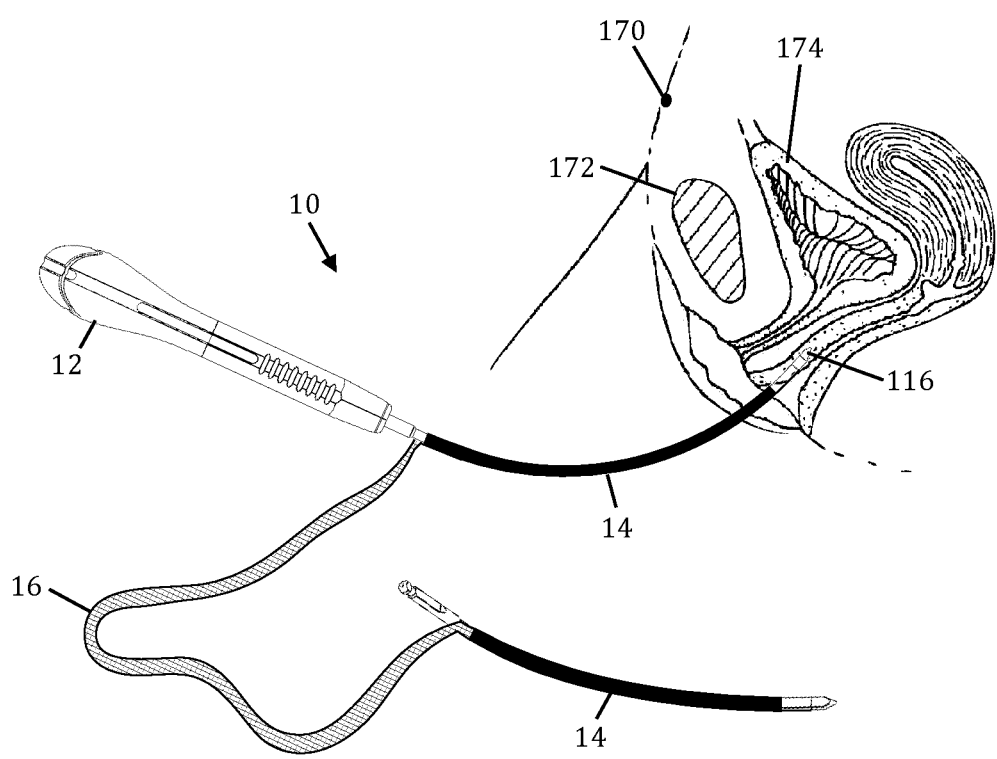

The user may then gently push the tip of the catheter/rigid guide toward the posterior lateral wall of the bladder opposite to the intended insertion path of the needle 14 (e.g., FIG. 37B). By way of example, pushing the catheter/rigid guide toward one side of the patient will elongate and displace the bladder away from the back of the pubic symphysis and position the bladder neck and urethra to allow passage of the needle 14 on the patient's opposite side with minimal risk of bladder perforation. Holding the handle assembly 12 in the dominant hand, the user may then pass the tip 116 of the needle 14 paraurethrally through the urogenital diaphragm at the level of the mid urethra, as shown by way of example only in FIGS. 38-39. The user may control the initial insertion of the device by using the tip of the index finger of the non-dominant hand placed in the vagina under the anterior vaginal wall, just lateral to the sub-urethral incision. The needle tip 116 should be oriented horizontal to the frontal plane during the initial submucosal passage in the periurethral dissected space. The tip 116 of the needle 14 may then be passed through the dissected space until it reaches the end of the dissected space.

Figure 40:
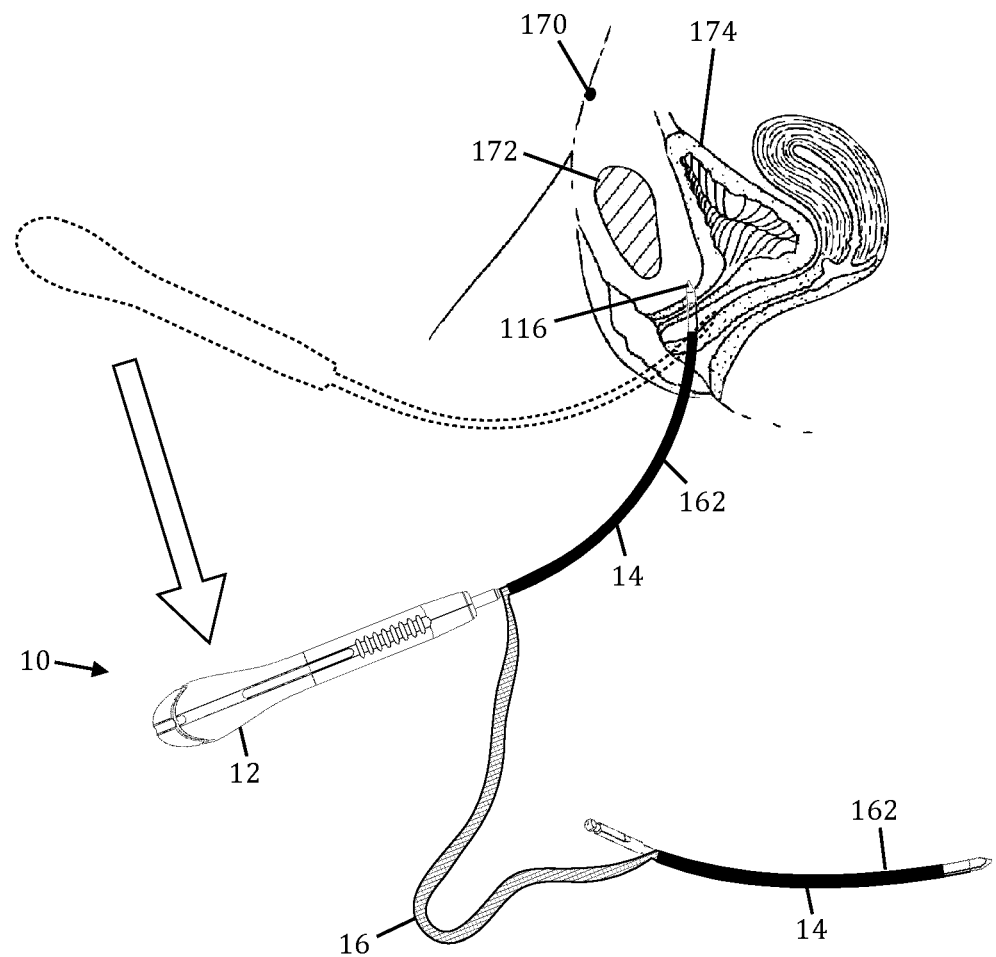

Immediately after perforation of the urogenital diaphragm, the handle assembly 12 may be maneuvered (e.g., lowered) to transition the position of the needle tip 116 from horizontal to vertical while remaining in close contact with the back of the pubic symphysis (e.g., FIG. 40). In some embodiments, the starting edge of the (preferably black, for example) needle sheath 162 may be used to assist with defining the proper depth of insertion when transitioning the orientation of the needle tip 116 from a horizontal to vertical position via lowering of the handle assembly 12.

Figure 41:
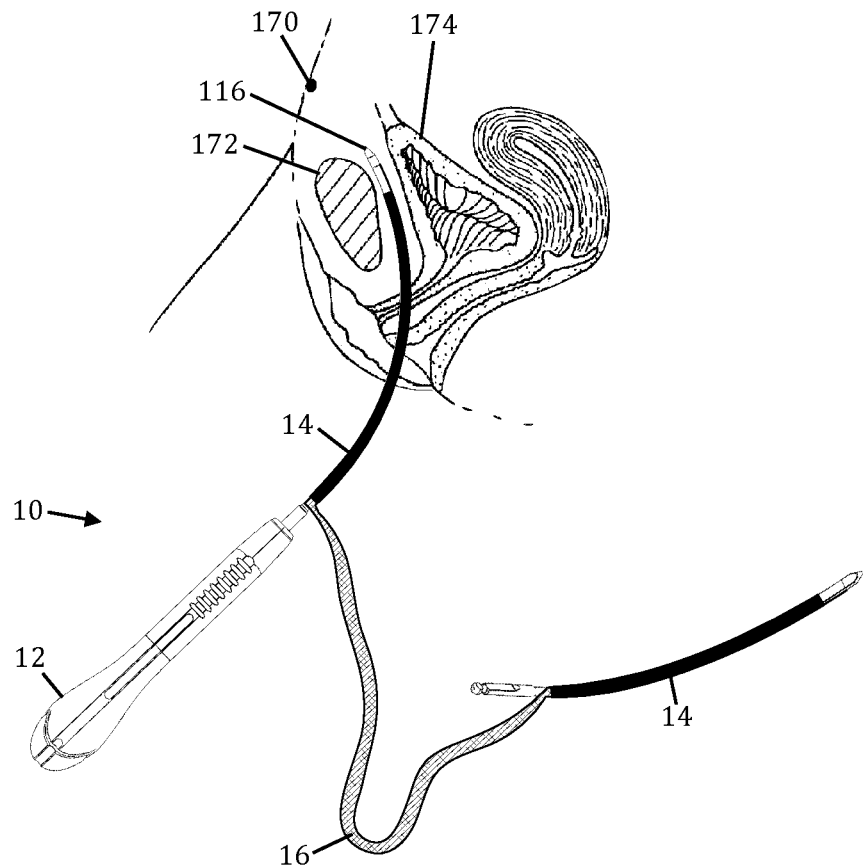
Figure 42:
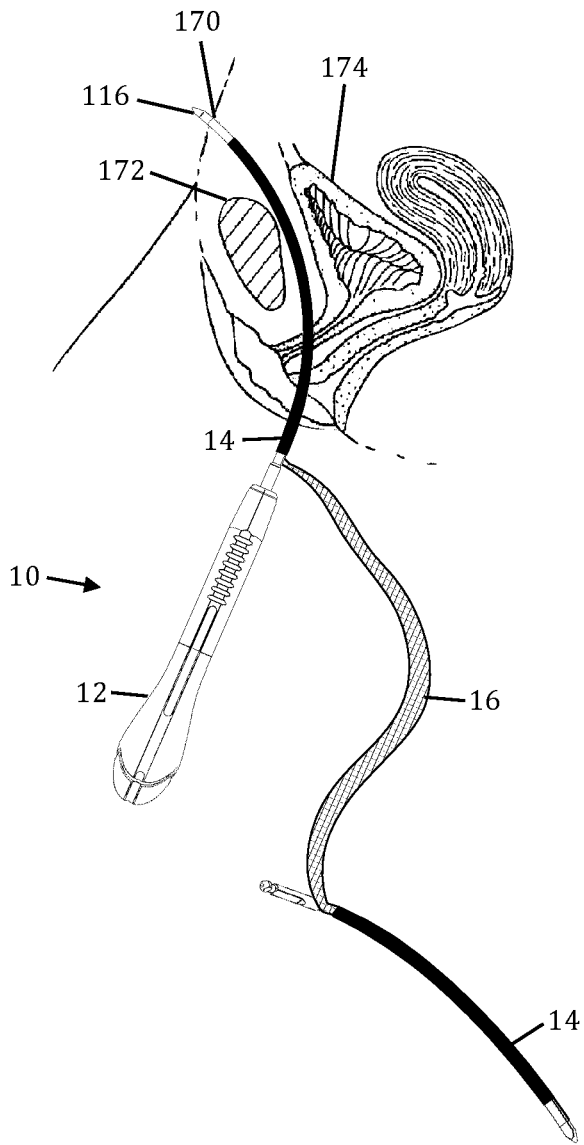
Figure 43:
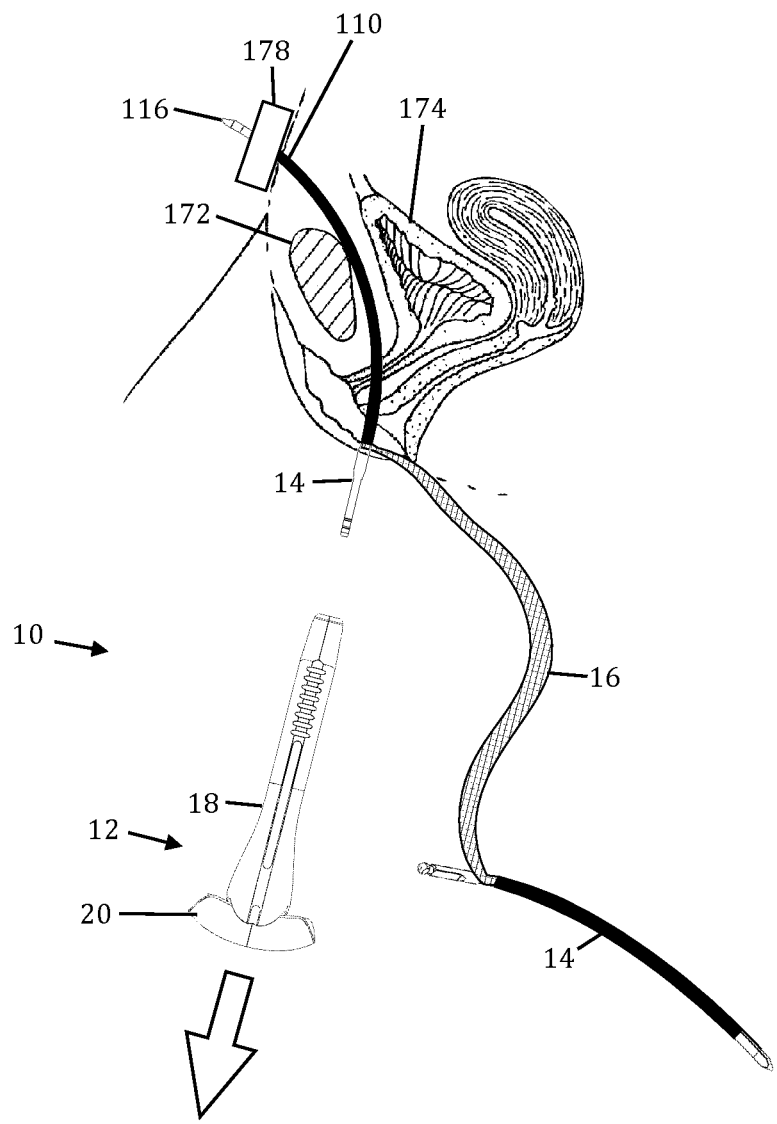
Figure 44:
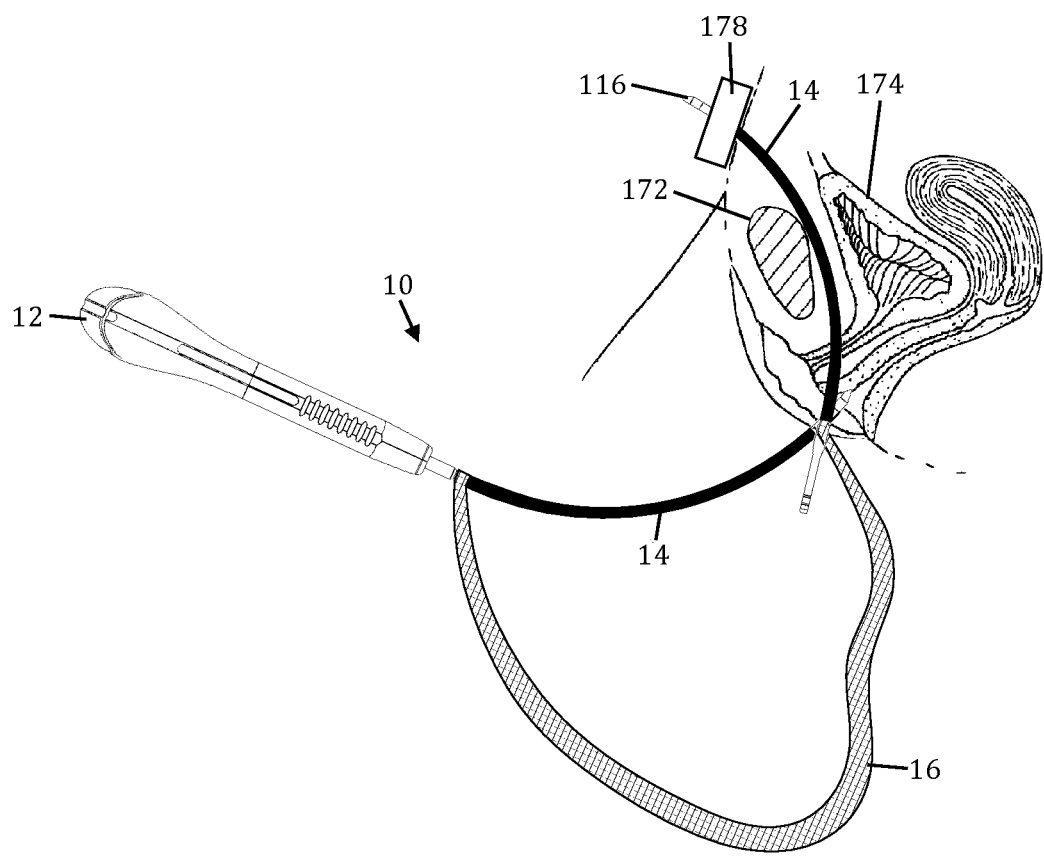

After passing the needle tip 116 through the urogenital diaphragm and into the retropubic space, resistance to the passage of the needle 14 is significantly reduced (e.g., FIG. 41). At this point the user may move the non-dominant hand from the vagina to the pre-marked suprapubic exit site 170. Keeping the handle assembly 12 low, the user may continue to advance the needle tip 116 in close contact with the pubic symphysis until the needle tip 116 passes through the rectus muscle and penetrates the skin at the exit site 170 (e.g., FIG. 42). The user may then advance the needle tip 116 a distance (e.g., approximately 5 cm) past the skin and place a clamp 178 on the needle shaft 110 to secure its position (e.g., FIG. 43). The needle 14 should not be advanced any further at this time. The user may then release the needle 14 from the handle assembly 12 by holding the handle body 18 and rotating the handle insert 20 counter clockwise one quarter turn (e.g., approximately 90°). The user may then secure the needle 14 coupled to the other end of the implant 16 to the handle assembly 12 and repeat the implant delivery steps on the opposite side of the urethra (see, e.g., FIG. 44). To reduce the risk of bladder injury, it may be important to displace the bladder to the contralateral side when using the rigid catheter.

Figure 45:
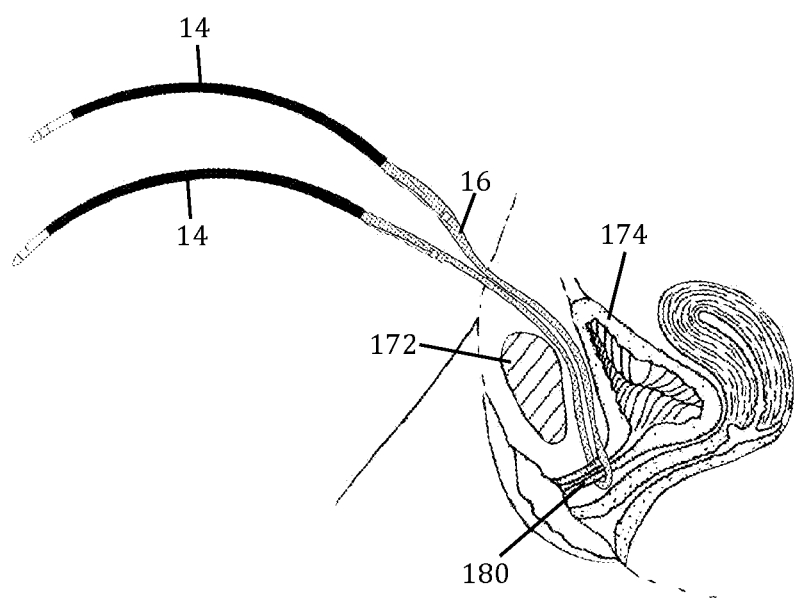

At this point, the implant 16 is inserted in the target space but not tensioned. Tensioning of the implant 16 may occur as follows. With both needles 14 clamped just above the skin, the catheter may be removed from the bladder and a cystoscopy may be performed to confirm bladder integrity (e.g., with a 70° lens). During cytoscopy, the dark color of the needle sheath 162 may be used to assist with visual confirmation of the needle location. Once bladder integrity has been confirmed, each needle 14 may be gently pulled upward and through the skin to position the mesh portion of the implant loosely under the mid urethra 180 (i.e. without tension; see, e.g. FIG. 45). By way of example, if using local anesthesia, patient feedback may be used (e.g., coughing with a full bladder, ~300 mL) to reduce urinary leakage to a few drops when under stress. At this point the user may cut the implant assembly (e.g., implant 16 and implant sheath 160) adjacent the needles 14 and remove each needle 14 such that only the implant 16 and implant sheath 160 remain. Premature removal of the needle 14 may make subsequent implant 16 adjustments difficult. Using a clamp, the user may grasp each implant sheath 160, while being careful to avoid clamping the implant. A blunt instrument (scissors, forceps) may be placed between the implant 16 and urethra to stabilize the implant 16 during implant sheath 160 removal. Each implant sheath 16 may be carefully removed one at a time by gently pulling the clamp away from the abdomen. The user may then complete any final implant tension adjustments (as applicable).

Once the implant sheath(s) 160 have been removed, the user may cut the abdominal ends of the implant 16 just below skin level and leave the ends in the subcutis, without suturing the implant 16. The vaginal and abdominal skin incisions may be closed using suture or surgical skin adhesive. Following this procedure, postoperative catheterization is not typically required to empty the bladder. Rather, the patient may be encouraged to try to empty their bladder 2-3 hours after the operation.

What is claimed is:

1. An implant delivery system for delivering a urethral sling implant to a surgical target site within a patient's pelvis during a retropubic midurethral sling procedure, comprising:
   a handle body comprising a proximal end, a distal end, a bulbous proximal portion including a proximal recess formed at the proximal end, an elongated distal portion extending distally from the bulbous proximal portion along a longitudinal axis and having a distal aperture at the distal end, and an axial lumen extending through the handle body along the longitudinal axis between the proximal recess and the distal aperture, the longitudinal axis defining a longitudinal direction;
   a handle insert having a proximal knob portion and an elongated extension extending distally from the proximal knob portion, the elongated extension having a distal end including a needle coupling element, the handle insert configured to reversibly couple with the handle body such that the elongated extension is received within the axial lumen and the proximal knob portion is received within the proximal recess; and
   a surgical needle having a proximal coupling element configured to removably couple with the handle insert, an implant coupling element configured to engage a surgical implant for delivery to a surgical target site, an elongated curvilinear shaft extending distally from the proximal coupling element, and a shaped distal tip configured to penetrate patient anatomy;
   wherein the elongated curvilinear shaft is curved in the longitudinal direction, and the elongated curvilinear shaft includes an arcuate surface extending along at least a portion of the curvilinear shaft, the arcuate surface having an arc component oriented in the longitudinal direction and a flat component oriented in a direction transverse to the longitudinal direction, and wherein the arcuate surface is dimensioned to contact a pubic symphysis during the retropubic midurethral sling procedure to provide at least one of tactile confirmation of needle orientation, visual confirmation of needle orientation, and improved needle tracking during an advancement of the needle into the patient along the pubic symphysis.

2. The implant delivery system of claim 1, wherein the distal aperture comprises a tapered needle interface.

3. The implant delivery system of claim 1, wherein the elongated curvilinear shaft of the surgical needle has a concave side and a convex side.

4. The implant delivery system of claim 3, wherein the arcuate surface is positioned on the concave side.

5. The implant delivery system of claim 4, wherein the elongated curvilinear shaft has a second arcuate surface on the convex side.

6. The implant delivery system of claim 1, wherein the handle insert is configured to be coupled with the handle body in a first rotational orientation that enables coupling of the proximal coupling element of the surgical needle with the needle coupling element of the handle insert through the distal aperture of the handle body, and thereafter rotated to a second rotational orientation wherein the surgical needle is securely coupled with the handle insert and the handle insert is securely coupled with the handle body.

7. The implant delivery system of claim 6, wherein the handle insert is non-threadedly rotated within the handle body.

8. The implant delivery system of claim 6, wherein the handle insert is rotated 90° in a clockwise direction to transition from the first rotational orientation to the second rotational orientation.

9. The implant delivery system of claim 6, wherein the handle insert is configured to produce at least one of audible and tactile feedback upon completing a transition from the first rotational orientation to the second rotational orientation.

10. The implant delivery system of claim 9, wherein the handle insert includes at least one deflectable member configured to forcibly deflect into a retention recess formed within the proximal recess upon completing a transition from the first rotational orientation to the second rotational orientation.

11. The implant delivery system of claim 1, further comprising a protective sheath covering a substantial portion of the elongated curvilinear shaft of the surgical needle, the surgical needle further comprising an unsheathed distal portion positioned between a distal end of the protective sheath and the shaped distal tip.

12. The implant delivery system of claim 11, wherein the unsheathed portion comprises a visual depth indicator.

13. The implant delivery system of claim 12, wherein the unsheathed portion has a length dimension within a range of 15 mm to 50 mm.

14. The implant delivery system of claim 11, wherein the sheath has a color that provides contrast with patient anatomy under cytoscopy.

15. The implant delivery system of claim 14, wherein the sheath is black.

16. The implant delivery system of claim 11, wherein the sheath is a non-removable overwrap applied to the needle.

17. An implant delivery system for delivering a urethral sling implant to a surgical target site within a patient's pelvis during a retropubic midurethral sling procedure, comprising:
 a handle member having an elongated shaft including a coupling element configured to removably couple with a surgical needle, and a longitudinal axis extending through the elongated shaft, the longitudinal axis defining a longitudinal direction;
 a surgical needle having a proximal coupling element configured to removably couple with the handle member, an implant coupling element configured to engage a surgical implant for delivery to a surgical target site, an elongated curvilinear shaft extending distally from the proximal coupling element, and a shaped distal tip configured to penetrate patient anatomy;
 wherein the elongated curvilinear shaft of the surgical needle is curved in the longitudinal direction, and the elongated curvilinear shaft includes an arcuate surface extending along at least a portion of the curvilinear shaft, the arcuate surface having an arc component oriented in the longitudinal direction and a flat component oriented in a direction transverse to the longitudinal direction, and
 wherein the arcuate surface is dimensioned to contact a pubic symphysis during the retropubic midurethral sling procedure to provide at least one of tactile confirmation of needle orientation, visual confirmation of needle orientation, and improved needle tracking during an advancement of the needle into the patient along the pubic symphysis.

18. The implant delivery system of claim 17, wherein the elongated curvilinear shaft of the surgical needle has a concave side and a convex side.

19. The implant delivery system of claim 18, wherein the arcuate surface is positioned on the concave side.

* * * * *